(12) United States Patent
Markovic et al.

(10) Patent No.: US 9,427,477 B2
(45) Date of Patent: Aug. 30, 2016

(54) CANCER TREATMENTS

(75) Inventors: Svetomir N. Markovic, Rochester, MN (US); Wendy K. Nevala, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/116,619

(22) PCT Filed: May 9, 2012

(86) PCT No.: PCT/US2012/037137
§ 371 (c)(1),
(2), (4) Date: Feb. 7, 2014

(87) PCT Pub. No.: WO2012/154861
PCT Pub. Date: Nov. 15, 2012

(65) Prior Publication Data
US 2014/0178486 A1 Jun. 26, 2014

Related U.S. Application Data

(60) Provisional application No. 61/609,689, filed on Mar. 12, 2012, provisional application No. 61/484,151, filed on May 9, 2011.

(51) Int. Cl.
| | |
|---|---|
| A61K 39/395 | (2006.01) |
| A61K 47/48 | (2006.01) |
| A61K 31/337 | (2006.01) |
| A61K 31/282 | (2006.01) |
| C07K 16/22 | (2006.01) |
| C07K 16/28 | (2006.01) |
| A61K 38/38 | (2006.01) |
| A61K 9/51 | (2006.01) |
| A61K 9/00 | (2006.01) |

(52) U.S. Cl.
CPC ....... *A61K 47/48384* (2013.01); *A61K 9/0019* (2013.01); *A61K 9/5169* (2013.01); *A61K 31/282* (2013.01); *A61K 31/337* (2013.01); *A61K 38/38* (2013.01); *A61K 39/3955* (2013.01); *A61K 47/48546* (2013.01); *A61K 47/48892* (2013.01); *C07K 16/22* (2013.01); *C07K 16/2887* (2013.01)

(58) Field of Classification Search
None
See application file for complete search history.

(56) References Cited

U.S. PATENT DOCUMENTS

| | | |
|---|---|---|
| 4,350,687 A | 9/1982 | Lipton et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,112,409 B2 | 9/2006 | Blumenthal et al. |
| 7,678,552 B2 | 3/2010 | Kornblith |
| 7,906,121 B2 | 3/2011 | Chang et al. |
| 8,119,129 B2 | 2/2012 | Jure-Kunkel et al. |
| 8,344,177 B2 | 1/2013 | Neri et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2009/0004118 A1 | 1/2009 | Nie et al. |
| 2010/0047234 A1 | 2/2010 | Markovic |
| 2010/0112077 A1* | 5/2010 | Desai .................. A61K 9/0019 424/499 |
| 2010/0172835 A1 | 7/2010 | Ruoslahti et al. |
| 2011/0097340 A1 | 4/2011 | Ramachandra et al. |
| 2011/0150902 A1 | 6/2011 | Markovic |
| 2012/0315273 A1 | 12/2012 | Markovic |
| 2014/0056909 A1 | 2/2014 | Markovic |
| 2014/0302017 A1 | 10/2014 | Markovic |

FOREIGN PATENT DOCUMENTS

| | | |
|---|---|---|
| EP | 1 913 947 | 4/2008 |
| JP | 2001-0072589 | 3/2001 |
| WO | WO 89/10398 | 11/1989 |
| WO | WO 99/00113 A1 | 1/1999 |
| WO | WO 99/51248 | 10/1999 |
| WO | WO 2004/096224 | 11/2004 |
| WO | WO 2008057562 | 5/2008 |
| WO | WO 2008/112987 | 9/2008 |
| WO | WO 2009/043159 | 4/2009 |

(Continued)

OTHER PUBLICATIONS

Boasberg et al (J Clinical Oncology, 2009, 27:No. 15S, abstract #9061).*
Concurrent Infusions (J Oncol Pract. Jul. 2008; 4(4): 171).*
Perez et al (Cancer, 2009, 115:119-127).*
Kottschade et al (Cancer 2011, 117:1704-1710, published online Nov. 8, 2010).*
Avastin® Roche drug label Sep. 2008.*
Abraxane® for Injectable Suspension drug label, Sep. 2009.*
Australian Office Action in Application No. 2008224929, issued Jun. 25, 2012, 3 pages.

(Continued)

*Primary Examiner* — Laura B Goddard
(74) *Attorney, Agent, or Firm* — Crowell & Moring LLP

(57) ABSTRACT

This document provides methods and materials related to treating cancer (e.g., skin cancer). For example, methods and materials relating to the use of a composition containing albumin-containing nanoparticle/antibody complexes (e.g., Abraxane®/anti-VEGF polypeptide antibody complexes) to treat cancer (e.g., skin cancer) are provided.

6 Claims, 17 Drawing Sheets

(56) References Cited

FOREIGN PATENT DOCUMENTS

| WO | WO 2009/055343 | 4/2009 |
|---|---|---|
| WO | WO 2010/003057 | 1/2010 |
| WO | WO 2010/017216 | 2/2010 |
| WO | WO 2012/048223 A1 | 4/2012 |

OTHER PUBLICATIONS

Australian Office Action in Application No. 2008224929, issued May 31, 2013, 3 pages.
European Office Action for Application No. 09774506.1, dated Nov. 13, 2012, 3 pages.
European Search Report for Application No. 09774506.1, dated Mar. 22, 2012, 12 pages.
European Search Report in Application No. 08743903.0, dated Feb. 7, 2011, 8 pages.
International Preliminary Report on Patentability for Application No. PCT/US2009/049511, issued Jan. 5, 2011, 6 pages.
International Preliminary Report on Patentability for PCT/US2012/037137 mailed Nov. 21, 2013, 5 pages.
International Preliminary Report on Patentability in PCT/US2008/057025, dated Sep. 24, 2009, 6 pages.
International Search Report and Written Opinion for Application No. PCT/US2008/057025, mailed Jul. 1, 2008, 11 pages.
International Search Report and Written Opinion for Application No. PCT/US2009/049511, mailed Feb. 2, 2010, 8 pages.
International Search Report and Written Opinion of international application No. PCT/US2012/037137 mailed Sep. 28, 2012, 5 pages.
United States Office Action in U.S. Appl. No. 12/295,834, Jan. 27, 2012, 9 pages.
United States Office Action in U.S. Appl. No. 12/295,834, mailed Sep. 9, 2011, 7 pages.
United States Office Action in U.S. Appl. No. 13/591,847, mailed Sep. 19, 2012, 10 pages.
United States Office Action in U.S. Appl. No. 13/591,847, mailed Feb. 19, 2013, 14 pages.
United States Office Action in U.S. Appl. No. 13/591,847, mailed Dec. 19, 2013, 28 pages.
United States Office Action in U.S. Appl. No. 12/979,105, mailed Oct. 5, 2012, 16 pages.
United States Office Action in U.S. Appl. No. 12/979,105, mailed Apr. 11, 2013, 23 pages.
Agarwal et al., "Flow Cytometric analysis of Th1 and Th2 cytokines in PBMCs as a parameter of immunological dysfunction in patients of Superficial Transitional cell carcinoma of bladdwe," *Cancer Immunol. Immunother.*, 2006, 55(6):734-743.
Agarwala et al., "Randomized phase III study of paclitaxel plus carboplatin with or without sorafenib as second-line treatment in patients with advanced melanoma," *J. Clin. Oncol.*, 2007, 25(18S):8510 (Abstract).
Anonymous, A Phase II, multicenter, randomized, double-blind placebo-controlled trial evaluating the efficacy and safety of bevacizumab in combination with carboplatin and paclitaxel chemotherapy for the first-line treatment of patients with metastatic melanoma, U.S. National Institutes of Health, 2007, 3 pages.
Anonymous, "Phase II trial of carboplatin, weekly paclitaxel and biweekly bevacizumab in patients with unresectable stage IV melanoma," U.S. National Institutes of Health, 2007, 4 pages.
Asadullah et al., "Interleukin-10 therapy—review of a new approach," *Pharmarcol Rev.*, 2003, 55(2):241-269.
Atkins et al., "High-dose recombinant interleukin-2 therapy in patients with metastatic melanoma: long-term survival update," *Cancer J Sci Am.*, 2000, 6 Suppl 1:S11-14.
Atkins, "Interleukin-2: clinical applications," *Semin Oncol.*, 2002, 29(3 Suppl 7):12-27.
Balch et al., "The new melanoma staging system," *Semin Cutan Med Surg.*, 2003, 22(1):42-54.
Baumgartner et al., "Melanoma induces immunosuppression by up-regulating FOXP3(+) regulatory T cells," *J Surg Res.*, 2007, 141(1): 72-77.

Belani et al., "Multicenter, randomized trial for stage IIIb or IV non-small-cell lung cancer using weekly paclitaxel and carboplatin followed by maintenance weekly paclitaxel or observation," *J. Clin. Oncol.*, 2003, 21:2933-2939.
Bolstad et al., "A comparison of normalization methods for high density oligonucleotide array data based on variance and bias," *Bioinformatics*, 2003, 19:185-193.
Cao et al., "Response of resistant melanoma to a combination of weekly paclitaxel and bevacizumab,"*Clin Transl Oncol*, 2007, 9:119-120.
Carson et al., "A phase 2 trial of a recombinant humanized monoclonal anti-vascular endothelial growth factor (VEGF) antibody in patients with malignant melanoma," Proceedings of the ASCO vol. 22, No. 2873, General Poster Session, Thirty-Ninth Annual Meeting of the American Society of Clinical Oncology, May 31-Jun. 3, 2003, Chicago, IL, 2 pages.
Carson et al., "A phase 2 trial of a recombinant humanized monoclonal anti-vascular endothelial growth factor (VEGF) antibody in patients with malignant melanoma," Proc. Am. Soc. Clin. Oncol. 22: Abstract 2873 (2003).
Celis, "Overlapping human leukocyte antigen class I/II binding peptide vaccine for the treatment of patients with stage IV melanoma: evidence of systemic immune dysfunction," *Cancer*, 110(1):203-214.
Chisholm et al., "Response to influenza immunisation during treatment for cancer," *Arch Dis Child*, 2001, 84(6):496-500
Chong and Morse "Combining cancer vaccines with chemotherapy," *Expert Opin Pharmacother.*, 2006, 6(16):2813-2820.
Demirkesen et al., "The correlation of angiogenesis with metastasis in primary cutaneous melanoma: a comparative analysis of microvessel density, expression of vascular endothelial growth factor and basic fibroblastic growth factor," *Pathology*, 2006, 38:132-137.
Denardo and Coussens, "Inflammation and breast cancer. Balancing immune response: crosstalk betweem adaptive and innate immune cells during breast cancer progression," *Breast Cancer Res.*, 2007, 9(4):212.
Desai et. al., "Increased antitumor activity, intratumor paclitaxel concentrations, and endothelial cell transport of cremophor-free, albumin-bound paclitaxel, ABI-007, compared with cremophor-based paclitaxel," Clin Cancer Res., 2006, 12(4):1317-24.
Dudek et al., "Autologous large multivalent immunogen vaccine in patients with metastatic melanoma and renal cell carcinoma," *Am. J. Clin. Oncol.*, Apr. 1, 2008, 31(2):173-181.
ElBayoumi and Torchilin, "Tumor-Targeted Nanomedicines: Enhanced Antitumor Efficacy In vivo of Doxorubicin-Loaded, Long-Circulating Liposomes Modified with Cancer-Specific Monoclonal Antibody," *Clin Cancer Res.*, 2009, 15(6):1973-1980.
Ellyard et al., "Th2-mediated anti-tumour immunity: friend or foe?" *Tissue Antigens*, 2007, 70(1):1-11.
Elsadek and Kratz, "Impact of albumin on drug delivery—New applications on the horizon," *J of Controlled Release*, 2011, 1-25.
Ferrara et al., "The biology of VEGF and its receptors," *Nat. Med.*, 2003, 9:669-676.
Folkman, J. "Angiogenesis in cancer, vascular, rheumatoid and other disease," *Nat. Med.*, 1995, 1, 27-31.
Fricke et al., "Vascular endothelial growth factor-trap overcomes defects in dendritic cell differentiation but does not improve antigen-specific immune responses," *Clin. Cancer Res.*, 2007, 13:4840-4848.
Gabrilovich et al., "Production of vascular endothelial growth factor by human tumors inhibits the functional maturation of dendritic cells," *Nat. Med.*, 1996, 2:1096-1103.
Gao et al., "In vivo cancer targeting and imaging with semiconductor quantum dots," *Nat Biotech*, 2004, 22(8):969-976.
Gogas et al., "Chemotherapy for metastatic melanoma: time for a change?" Cancer, 2007, 109(3): 455-464.
Graells et al., "Overproduction of $VEGF_{165}$ concomitantly expressed with its receptors promotes growth and survival of melanoma cells through MAPK and PI3K signaling," *J. Invest. Dermatol.*, 2004, 123:1151-1161.

(56) References Cited

OTHER PUBLICATIONS

Haley and Frenkel, "Nanoparticles for drug delivery in cancer treatment," *Urol. Oncol.: Seminars and Original Invest.*, 2008, 26:57-64.
Hauschild et al., "Individualized therapy of disseminated cancer using malignant melanoma as a model," Cancer and Metastasis Reviews, 2006, 25(2): 253-256.
Hersh et al., "Open-label, multicenter, phase II trial of ABI-007 in previously treated and previously untreated patients with metastatic malignant melanoma," *J. Clin. Oncol.*, 2005, 23(16S):7558 (Abstract).
Hodi et al., "Phase II study of paclitaxel and carboplatin for malignant melanoma," *Am. J. Clin. Oncol.*, 2002, 25:283-286.
Huncharek et al., "Single-agent DTIC versus combination chemotherapy with or without immunotherapy in metastatic melanoma: a meta-analysis of 3273 patients from 20 randomized trials," Melanoma Research, 11:75-81 (2001).
Inagaki et al., "Clinical significance of serum Th1-, Th2- and regulatory T cells-associated cytokines in adult T-cell leukemia/lymphoma: High interleukin-5 and -10 levels are significant unfavorable prognostic factors," *Int. J. Cancer*, 2006, 118(12):3054-3061.
Jiang and Chess, "Regulation of immune responses by T cells," N Engl J Med., 2006, 354(11): 1166-1176.
Kamat et al., "Metronomic chemotherapy enhances the efficacy of antivascular therapy in ovarian cancer," *Cancer Res.*, 2007, 67(1):281-288.
Kawai et al., "VEGF121 promotes lymphangiogenesis in the sentinel lymph nodes of non-small cell lung carcinoma patients," *Lung Cancer*, 2008, 59(1):41-47.
Kikuchi et al., "Vascular endothelial growth factor and dendritic cells in human squamous cell carcinoma of the oral cavity," *Anticancer Res.*, 2006, 26(3A):1833-1848.
Kirkwood et al., "A pooled analysis of eastern cooperative oncology group and intergroup trials of adjuvant high-dose interferon for melanoma," Clin Cancer Res., 2004, 10(5):1670-1677.
Korman et al., "Tumor immunotherapy: preclinical and clinical activity of anti-CTLA4 antibodies," Curt Opin Invest Drugs, 2005, 6(6):582-591.
Krishnan et al., "Programmed death-1 receptor and interleukin-10 in liver transplant recipients at high risk for late cytomegalovirus disease," *Transpl Infec Dis.*, 12(4):363-70, print Aug. 2010, ePub Jan. 2010.
Kukowska-Latallo et al., "Nanoparticle Targeting of Anticancer Drug Improves Therapeutic Response in Animal Model of Human Epithelial Cancer," *Cancer Res*, 2005, 65(12):5317-5324.
Kumar et al., "Th1/Th2 cytokine imbalance in meningioma, anaplastic astrocytoma and glioblastoma multiforme patients," *Oncol. Rep.*, 2006, 15(6):1513-1516.
Lau et al., "Is inhibition of cancer angiogenesis and growth by paclitaxel schedule dependent?" *Anti-Cancer Drugs*, 2004, 15:871-875.
Lei et al., "Comparing cellular uptake and cytotoxicity of targeted drug carriers in cancer cell lines with different drug resistance mechanisms," *Nanomed: Nanotech, Biol, and Med.*, 2011, 7:324-332.
Lev et al., "Dacarbazine causes transcriptional up-regulation of interleukin 8 and vascular endothelial growth factor in melanoma cells: a possible escape mechanism from chemotherapy," *Mol. Cancer Ther.*, 2003, 2:753-763.
Lev et al., "Exposure of melanoma cells to dacarbazine results in enhanced tumor growth and metastasis in vivo," *J. Clin. Oncol.*, 2004, 22:2092-2100.
Marcoval et al., "Angiogenesis and malignant melanoma. Angiogenesis is related to the development of vertical (tumorigenic) growth phase," *J. Cutan. Pathol.*, 1997, 24:212-218.
Markovic et al., "A phase II study of ABT-510 (thrombospondin-1 analog) for the treatment of metastatic melanoma," *Am. J. Clin. Oncol.*, 2007, 30(3):303-309.

Markovic et al., "A reproducible method for the enumeration of functional (cytokine producing) versus non-functional peptide-specific cytotoxic T lymphocytes in human peripheral blood," *Clin. Exp. Immunol.*, 2006, 145:438-447.
Markovic et al., "Peptide vaccination of patients with metastatic melanoma: improved clinical outcome in patients demonstrating effective immunization," *Am J Clin Oncol.*, 2006, 29(4):352-360.
Matsuda et al., "Preoperative oral immune-enhancing nutritional supplementation corrects TH1/TH2 imbalance in patients undergoing elective surgery for colorectal cancer," *Dis. Colon Rectum*, 2006, 49(4):507-516.
McElroy et al., "Imaging of Primary and Metastatic Pancreatic Cancer Using a Fluorophore-Conjugated Anti-CA19-9 Antibody for Surgical Navigation," *World J Surg.*, 2008, 32:1057-1066.
Melcher, "Recommendations for influenza and pneumococcal vaccinations in people receiving chemotherapy," *Clin Oncol (R Coll Radiol)*, 2005, 17(1): 12-15.
Merchan et al., "Increased endothelial uptake of paclitaxel as a potential mechanism for its antiangiogenic effects: potentiation by Cox-2 inhibition," *Int. J. Cancer*, 2005, 113:490-498.
Middleton et al., "Randomized phase III study of temozolomide versus dacarbazine in the treatment of patients with advanced metastatic malignant melanoma," *J. Clin. Oncol.*, 2000, 18:158-166.
Mimura et al., "Vascular endothelial growth factor inhibits the function of human mature dendritic cells mediated by VEGF receptor-2," *Cancer Immunol Immunother.*, 2007, 56(6):761-770.
Mocellin et al., "Cytokines and immune response in the tumor microenvironment," *J Immunother.*, 2001, 24(5):392-407.
Motl, S., "Bevacizumab in combination chemotherapy for colorectal and other cancers," *Am. J. Health-Syst. Pharm*, 2005, 62:1021-1032.
Ng et al., "Influence of formulation vehicle on metronomic taxane chemotherapy: albumin-bound versus cremophor EL-based paclitaxel," *Clin. Cancer Res.*, 2006, 12:4331-4338.
Ng et al., "Taxane-mediated antiangiogenesis in vitro: influence of formulation vehicles and binding proteins," *Cancer Res.*, 2004, 64:821-824.
Oku et al., "Tumor growth modulation by sense and antisense vascular gene expression: effects on angiogenesis, vascular permeability, blood volume, blood flow, fluorodeoxyglucose uptake, and proliferation of human melanoma intracerbral xenografts," *Cancer Res.*, 1998, 58:4185-4192.
Parikh and Ellis, "The vascular endothelial growth factor family and its receptors," *Hematol. Oncol. Clin. N. Am.*, 2004, 18:951-971.
Park et al., "Anti-HER2 Immunoliposomes: Enhanced Efficacy Attributable to Targeted Delivery," *Clin. Cancer Res.*, 2002, 8:1172-1181.
Perez et al., "Phase 2 trial of carboplatin, weekly paclitaxel, and biweekly bevacizumab in patients with unresectable stage IV melanoma: a north central cancer treatment group study," Cancer, 2009, 115(1): 119-127.
Phase II: A Study of Bevacizumab With Carboplatin and Paclitaxel Chemotherapy for the First-Line Treatment of Patients With Metastatic Melanoma (BEAM) Mar. 12, 2007, [retrieved Mar. 15, 2010]. Retrieved from the Internet: <URL: http://clinicaltrials.gov/archive/NCT00434252/2007_03_12>, 3 pages.
Polak et al., "Mechanisms of local immunosuppression in cutaneous melanoma," *Br J Cancer*, 2007, 96(12):1879-1887.
Porrata and Markovic, "Timely reconstitution of immune competence affects clinical outcome following autologous stem cell transplantation," *Clin Exp Med.*, 2004, 4(2):78-85.
Porrata et al., "Early lymphocyte recovery predicts superior survival after stem autologous hematoppietic stem cell transplantation in multiple myeloma or non-Hodgkin lymphoma," *Blood*, 2001, 98(3):579-585.
Powell et al., "Adoptive transfer of vaccine-induced peripheral blood mononuclear cells to patients with metastatic melanoma following lymphodepletion," *J Immunol.*, 2006, 177(9):6527-6539.
Pries and Wollenberg, "Cytokines in head and neck cancer," *Cytokine Growth Factor Rev.*, 2006, 17(3):141-146.

(56) References Cited

OTHER PUBLICATIONS

Ranieri et al., "Vascular endothelial growth factor (VEGF) as a target of bevacizumab in cancer: from the biology to the clinic," *Curr. Med. Chem.*, 2006, 13:1845-1857.
Rao et al., "Combination of paclitaxel and carboplatin as second-line therapy for patients with metastatic melanoma," *Cancer*, 2006, 106:375-382.
Ribas et al., "Antitumor activity in melanoma and anti-self responses in a phase I trial with the anti-cytotoxic T lymphocyte-associated antigen 4 monoclonal antibody CP-675,206" *J Clin Oncol.*, 2005, 23(35):8968-8977.
Rosenberg et al., "Tumor progression can occur despite the induction of very high levels of self/tumor antigen-specific CD8+ T cells in patients with melanoma," *J. Immunol.*, 2005, 175(9):6169-6176.
Roy et al., "Tumor associated release of interleukin-10 alters the prolactin receptor and down-regulates prolactin responsiveness of immature cortical thymocytes," *J Neuroimmunol.*, 2007, 186(1-2):112-120.
Salven et al., "Enhanced expression of vascular endothelial growth factor in metastatic melanoma," *Br. J. Cancer*, 1997, 76:930-934.
Sandler et al., "Paclitaxel-carboplatin alone or with bevacizumab for non-small-cell lung cancer," *N. Engl. J. Med.*, 2006, 355:2542-2550.
Sato et al., "Intraepithelial CD8+ tumor-infiltrating lymphocytes and a high CD8+/regulatory T cell ratio are associated with favorable prognosis in ovarian cancer," *Proc Natl Aead Sci USA*, 2005, 102(51):18538-18543.
Sester et al., Differences in CMV-specific T-cell levels and long-term susceptibility to CMV infection after kidney, heart and lung transplantation, *Am J Transplant.*, 5(6):1483-1489, Jun. 2005.
Srivastava et al., "Angiogenesis in cutaneous melanoma: pathogenesis and clinical implications," *Microsc. Res. Tech.*, 2003, 60:208-224.
Streit and Detmar, "Angiogenesis, lymphangiogenesis, and melanoma metastasis," *Oncogene*, 2003, 22:3172-3179.
Taieb et al., "Chemoimmunotherapy of tumors: Cyclophosphamide synergtizes with exoxome based vaccines," *J. Immunol.*, Mar. 1, 2006, 176(5):2722-2729.
Tao et al , "Inhibiting the growth of malignant melanoma by blocking the expression of vascular endothelial growth factor using an RNA interference approach," *Br. J. Dermatol.*, 2005, 153:715-724.
Tas et al., "Circulating serum levels of angiogenic factors and vascular endothelial growth factor receptors 1 and 2 in melanoma patients," *Melanoma Res.*, 2006, 16:405-411.
Terheyden et al., "Anti-vascular endothelial growth factor antibody bevacizumab in conjunction with chemotherapy in metastasizing melanoma," *Journal of Cancer Research and Clinical Oncology*, 2007, 133(11): 897-901.
Ugurel et al., "Increased serum concentration of angiogenic factors in malignant melanoma patients correlates with tumor progression and survival," *J. Clin. Oncol.*, 2001, 19:577-583.
Vacca et al., "Docetaxel versus paclitaxel for antiangiogenesis," *J. Hematother. Stem Cell Res.*, 2002, 11:103-118.
Varker et al., "A randomized phase 2 trial of bevacizumab with or without daily low-dose interferon alfa-2b in metastatic malignant melanoma," *Ann Surg Oncol.*, 14(8):2367-2376, print Aug. 2007, Epub May 2007.
Vence et al., "Circulating tumor antigen-specific regulatory T cells in patients with metastatic melanoma," *Proc Natl Acad Sci USA*, 2007, 104(52): 20884-20889.
Walker and Disis, "Monitoring immune responses in cancer patients receiving tumor vaccines," *Int Rev Immunol.*, 2003, 22(3-4):283-319.
Wang et al., "Biofunctionalized targeted nanoparticles for therapeutic applications," *Expert Opin. Biol. Ther.*, 2008, 8(8):1063-1070.
Wang et al., "Paclitaxel at ultra low concentrations inhibits angiogenesis without affecting cellular microtubule assembly," *Anti-Cancer Drugs*, 2003, 14:13-19.
Weber, "Review: anti-CTLA-4 antibody ipilimumab: case studies of clinical response and immune-related adverse events," *Oncologist*, 12(7):864-872, Jul. 2007.
Wong et al., "Programmed death-1 blockade enhances expansion and functional capacity of human melanoma antigen-specific CTLs," *Int. Immunol.*, 2007, 19:1223-1234.
Yee et al., "Adoptive T cell therapy using antigen-specific CD8+ T cell clones for the treatment of patients with metastatic melanoma: in vivo persistence, migration, and antitumor effect of transferred T cells," *Proc Natl Acad Sci USA*, 2002, 99(25):16168-16173.
Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)," *Melanoma Res.*, 2003, 13:531-536.
Davis, "Affinity seperation of antibody-toxin conjugate from albumin-stabilized formulation," *Am Biotechnol Lab.*, 12(4):60-64, Mar. 1994.
de Weers et al., "Daratumumab, a novel therapeutic human CD38 monoclonal antibody, induces killing of multiple myeloma and other hematological tumors," *J. Immunol.*, 186(3): 1840-1848, Feb. 1, 2011.
Kondejewski et al., "Synthesis and characterization of carbohydrate-linked murine monoclonal antibody K20-human serum albumin conjugates," *Bioconjug Chem.*, 5(6):602-611, Nov.-Dec. 1994.
Kratz and Beyer, "Serum proteins as drug carriers of anticancer agents: a review," *Drug Deliv.*, 5(4):281-299, 1998.
Kratz, "Albumin as a drug carrier: design of prodrugs, drug conjugates and nanoparticles," *J Control Release.*, 132(3):171-183, Epub May 17, 2008.
Wagner et al., "Enhanced drug targeting by attachment of an anti alphav integrin antibody to doxorubicin loaded human serum albumin nanoparticles," *Biomaterials.*, 31(8):2388-2398, Epub Dec. 23, 2009.
European Search Report for Application No. 12781802.9 dated Dec. 18, 2014, 7 pages.
Office Action in U.S. Appl. No. 14/051,849 mailed Dec. 19, 2014, 15 pages.
Office Action in U.S. Appl. No. 14/309,617, mailed Oct. 1, 2014, 14 pages.
International Preliminary Report on Patentability for PCT/US2013/062638, mailed Apr. 16, 2015, 11 pages.
International Search Report and Written Opinion for PCT/US2013/062638, mailed Jan. 23, 2014, 19 pages.
Australian Office Action issued in counterpart Australian Application No. 2012253571 dated Jun. 10, 2016 (four (4) pages).

\* cited by examiner

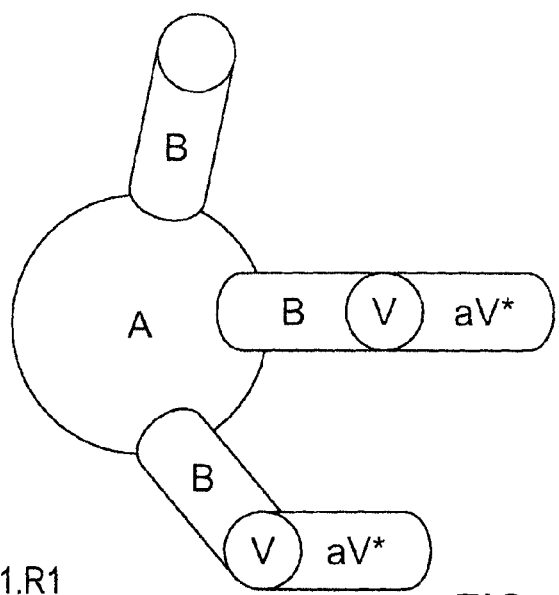
FIG. 1
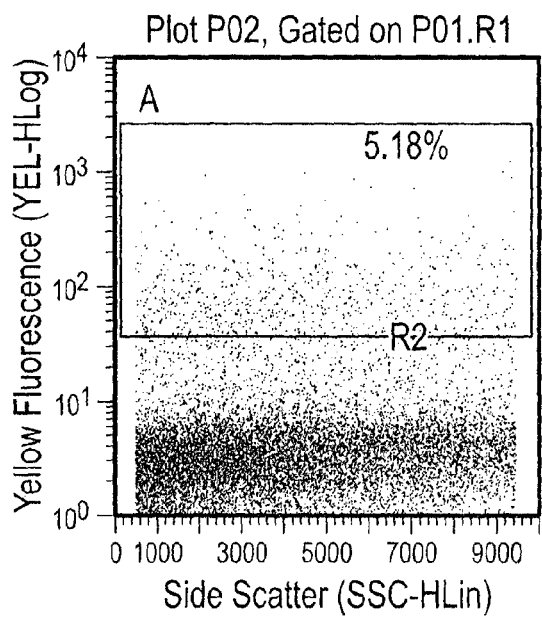
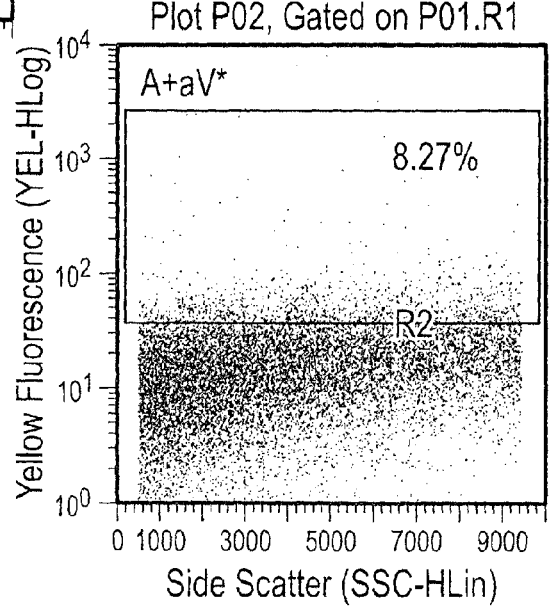
FIG. 2

CANCER TREATMENTS

CROSS-REFERENCE TO RELATED APPLICATIONS

This application is a National Stage application under 35 U.S.C. §371 of International Application No. PCT/US2012/037137, having an International Filing Date of May 9, 2012, which claims the benefit of U.S. Provisional Application Ser. No. 61/609,689, filed Mar. 12, 2012, and U.S. Provisional Application Ser. No. 61/484,151, filed May 9, 2011. The disclosures of the prior applications are considered part of (and are incorporated by reference in) the disclosure of this application.

BACKGROUND

1. Technical Field

This document relates to methods and materials involved in treating cancer (e.g., skin cancers such as melanoma). For example, this document relates to methods and materials involved in using complexes containing albumin-containing nanoparticles (e.g., Abraxane® nanoparticles) and antibodies (e.g., anti-VEGF polypeptide antibodies such as Avastin®) to treat cancer. This document also relates to methods and materials involved in using Abraxane® in combination with an anti-VEGF polypeptide antibody (e.g., Avastin®) to treat skin cancer.

2. Background Information

Melanoma is the most serious form of skin cancer. It is a malignant tumor that originates in melanocytes, the cells which produce the pigment melanin that colors skin, hair, and eyes and is heavily concentrated in most moles. While it is not the most common type of skin cancer, melanoma underlies the majority of skin cancer-related deaths. About 48,000 deaths worldwide are registered annually as being due to malignant melanoma. Worldwide, there are about 160,000 new cases of melanoma each year. Melanoma is more frequent in white men and is particularly common in white populations living in sunny climates. Other risk factors for developing melanoma include a history of sunburn, excessive sun exposure, living in a sunny climate or at high altitude, having many moles or large moles, and a family or personal history of skin cancer. Melanomas fall into four major categories. Superficial spreading melanoma can travel along the top layer of the skin before penetrating more deeply. Lentigo maligna typically appears as a flat or mildly elevated mottled tan, brown, or dark brown discoloration and is found most often in the elderly. Nodular melanoma can occur anywhere on the body as a dark, protuberant papule or a plaque that varies from pearl to gray to black. Acral-lentiginous melanoma, although uncommon, is the most common form of melanoma in blacks. It can arise on palmar, plantar, or subungual skin. Metastasis of melanoma occurs via lymphatics and blood vessels. Local metastasis results in the formation of nearby satellite papules or nodules that may or may not be pigmented. Direct metastasis to skin or internal organs can occur.

SUMMARY

This document provides methods and materials involved in treating cancer (e.g., skin cancers such as melanoma). For example, this document provides methods and materials for using complexes containing albumin-containing nanoparticles (e.g., Abraxane® nanoparticles) and antibodies (e.g., anti-VEGF polypeptide antibodies such as Avastin®) to treat cancer. This document also provides methods and materials involved in using Abraxane® in combination with an anti-VEGF polypeptide antibody (e.g., Avastin®) to treat skin cancer (e.g., melanoma). Abraxane® is available from Celgene Corp. and is a nanoparticle formulation that combines paclitaxel with human albumin. Avastin® is also known as bevacizumab and is available from Genentech Corp. and Roche Corp. Avastin® is a humanized monoclonal antibody that binds to vascular endothelial growth factor A. As described herein, in vitro mixing of albumin-containing nanoparticles (e.g., Abraxane® nanoparticles) and antibodies (e.g., bevacizumab, bevacizumab, trastuzamab, or rituxan) can result in the formation of macromolecular complexes, the characteristics of which (e.g., size, antibody content, or chemotherapeutic drug content) can be customized depending on need. In some cases, such macromolecular complexes can retain antibody mediated target binding specificity, can retain or exhibit enhanced chemotherapeutic tumor cell cytotoxicity, and can exhibit no additional toxicity beyond that of Abraxane® nanoparticles alone. As also described herein, contacting Abraxane® with an anti-VEGF polypeptide antibody (e.g., Avastin®) prior to administration to a human (e.g., a human melanoma cancer patient) can result in a complex that, when administered as a complex, has an increased ability to treat melanoma as compared to a treatment regimen that includes administering Abraxane® and the anti-VEGF polypeptide antibody separately in a manner that does not form Abraxane®/anti-VEGF polypeptide antibody complexes.

The methods and materials provided herein can be used to increase the progression-free survival rate in skin cancer patients. Increasing progression-free survival can allow skin cancer patients to live longer.

In general, one aspect of this document features a method for treating a mammal having skin cancer. The method comprises, or consists essentially of, administering to the mammal a composition containing Abraxane®/anti-VEGF polypeptide antibody complexes (or complexes of (a) an anti-VEGF polypeptide antibody and (b) human albumin-containing nanoparticles having an agent other than placitaxel) under conditions wherein the length of progression-free survival is increased. The mammal can be a human. The skin cancer can be melanoma. The skin cancer can be stage IV melanoma. In some cases, a composition comprising Abraxane®/Avastin® complexes can be administered to the mammal. The composition can comprise an alkylating agent. The alkylating agent can be a platinum compound. The platinum compound can be carboplatin. The anti-VEGF polypeptide antibody can be a humanized antibody. The anti-VEGF polypeptide antibody can be bevacizumab. The composition can be administered by injection. The progression-free survival can be increased by 25 percent. The progression-free survival can be increased by 50 percent. The progression-free survival is increased by 75 percent. The progression-free survival can be increased by 100 percent. The composition can be administered under conditions wherein the time to progression is increased.

In another aspect, this document features a method for treating a mammal having cancer. The method comprises, or consists essentially of, administering, to the mammal, a composition comprising albumin-containing nanoparticle/antibody complexes, wherein the average diameter of the complexes is greater than 1 µm (e.g., between 1.1 µm and 5 µm, between 1.5 µm and 5 µm, between 4.5 and 20 µm, or between 5 and 20 µm). The mammal can be a human. The cancer can be skin cancer. The skin cancer can be melanoma. The skin cancer can be stage IV melanoma. The albumin-containing nanoparticle/antibody complexes can be Abraxane®/Avastin® complexes. The composition or the albumin-containing nanoparticle/antibody complexes can comprise an alkylating agent. The alkylating agent can be a platinum compound. The platinum compound can be carboplatin. The antibodies of the albumin-containing nanoparticle/antibody complexes can be anti-VEGF polypeptide antibodies. The anti-VEGF polypeptide antibodies can be humanized antibodies. The anti-VEGF polypeptide antibodies can be bevacizumab. The composition can be administered by injection. The administration of the composition can be effective to increase progression-free survival by 25 percent. The administration of the composition can be effective to increase progression-free survival by 50 percent. The administration of the composition can be effective to increase progression-free survival by 75 percent. The administration of the composition can be effective to increase progression-free survival by 100 percent. The administration of the composition can be under conditions wherein the median time to progression for a population of mammals with the cancer is at least 150 days. The administration of the composition can be under conditions wherein the median time to progression for a population of mammals with the cancer is at least 165 days. The administration of the composition can be under conditions wherein the median time to progression for a population of mammals with the cancer is at least 170 days. The average diameter of the complexes can be from 1.1 µm to 5 µm. The average diameter of the complexes can be from 2 µm to 5 µm. The average diameter of the complexes can be from 3 µm to 5 µm. The average diameter of the complexes can be from 5 µm to 50 µm. The average diameter of the complexes can be from 10 µm to 50 µm. The average diameter of the complexes can be from 5 µm to 25 µm.

In another aspect, this document features a method for treating a mammal having cancer. The method comprises, or consists essentially of, administering, to the mammal, a composition comprising albumin-containing nanoparticle/antibody complexes, wherein the average diameter of at least 5 percent of the complexes of the composition is greater than 1 µm. The mammal can be a human. The cancer can be skin cancer. The skin cancer can be melanoma. The skin cancer can be stage IV melanoma. The albumin-containing nanoparticle/antibody complexes can be Abraxane®/Avastin® complexes. The composition or the albumin-containing nanoparticle/antibody complexes can comprise an alkylating agent. The alkylating agent can be a platinum compound. The platinum compound can be carboplatin. The antibodies of the albumin-containing nanoparticle/antibody complexes can be anti-VEGF polypeptide antibodies. The anti-VEGF polypeptide antibodies can be humanized antibodies. The anti-VEGF polypeptide antibodies can be bevacizumab. The composition can be administered by injection. The administration of the composition can be effective to increase progression-free survival by 25 percent. The administration of the composition can be effective to increase progression-free survival by 50 percent. The administration of the composition can be effective to increase progression-free survival by 75 percent. The administration of the composition can be effective to increase progression-free survival by 100 percent. The administration of the composition can be under conditions wherein the median time to progression for a population of mammals with the cancer is at least 150 days. The administration of the composition can be under conditions wherein the median time to progression for a population of mammals with the cancer is at least 165 days. The administration of the composition can be under conditions wherein the median time to progression for a population of mammals with the cancer is at least 170 days. The average diameter of at least 5 percent of said complexes of said composition can be from 1.1 µm to 5 µm. The average diameter of at least 5 percent of said complexes of said composition can be from 2 µm to 5 µm. The average diameter of at least 5 percent of said complexes of said composition can be from 3 µm to 5 µm. The average diameter of at least 5 percent of said complexes of said composition can be from 5 µm to 50 µm. The average diameter of at least 5 percent of said complexes of said composition can be from 10 µm to 50 µm. The average diameter of at least 5 percent of said complexes of said composition can be from 5 µm to 25 µm. The average diameter of at least 10 percent of said complexes of said composition can be greater than 1 µm. The average diameter of at least 50 percent of said complexes of said composition can be greater than 1 µm. The average diameter of at least 75 percent of said complexes of said composition can be greater than 1 µm. The average diameter of at least 90 percent of said complexes of said composition can be greater than 1 µm.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a diagram of an Abraxane® nanoparticle (labeled A) complexed with an anti-VEGF polypeptide antibody (bevacizumab; labeled B). In two of the three cases, the anti-VEGF polypeptide antibody is shown binding to a VEGF-A polypeptide (labeled V), and a fluorescently-labeled anti-VEGF antibody (labeled aV*) is shown bound to the VEGF-A polypeptide.

In FIG. 4, 100 ng VEGF was used to visualize the complex.

FIG. 17 contains graphs of the size distributions of the indicated complexes incubated for one hour at room temperature.

DETAILED DESCRIPTION

Figure 2:
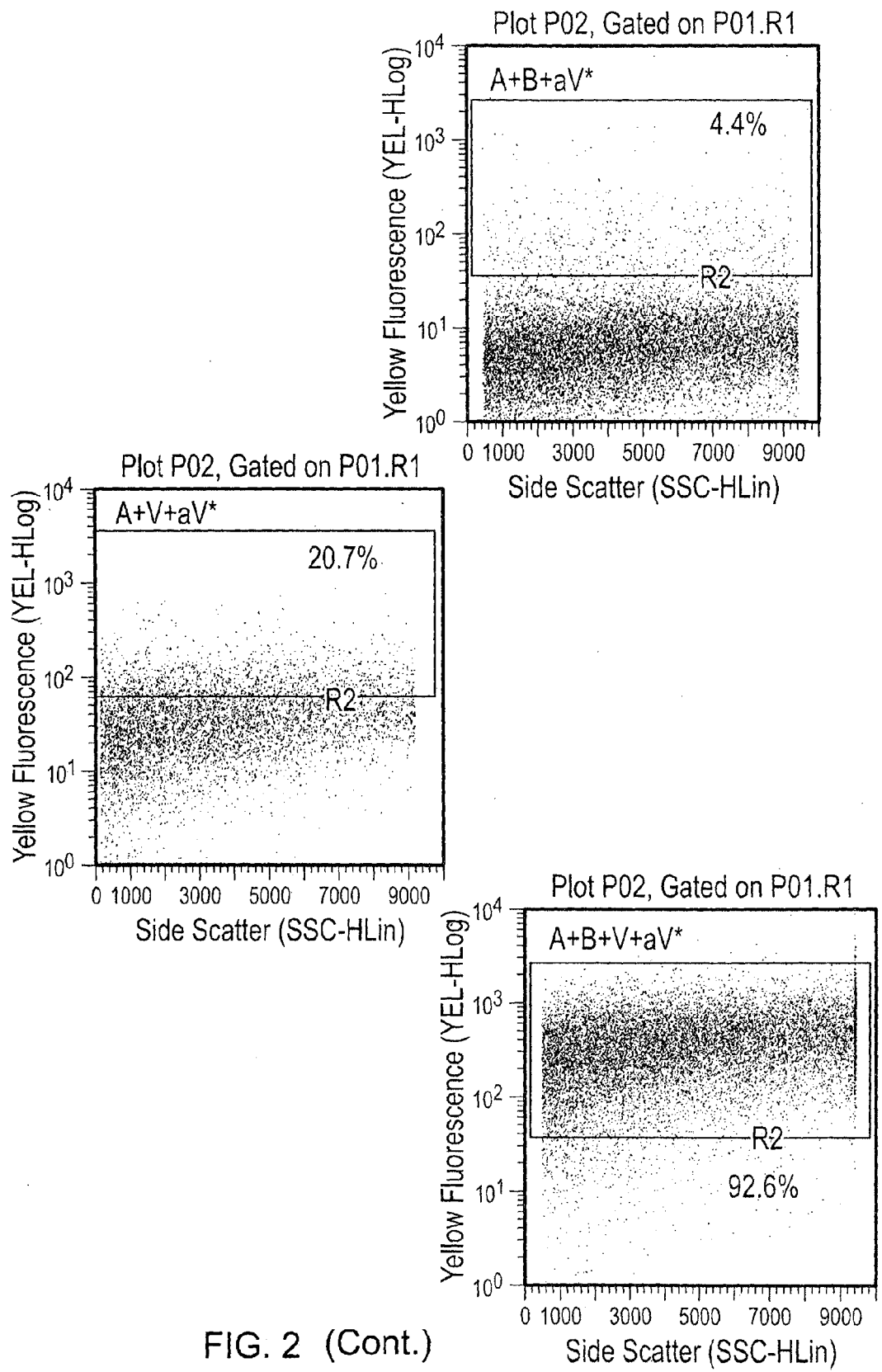
FIG. 2 contains scatter plots of a flow cytometry analysis plotting the level of yellow fluorescence of A alone, A plus aV*, A plus B plus aV*, A plus V plus aV*, or A plus B plus V plus aV*. The labels are as indicated in FIG. 1. These results demonstrate that A and B spontaneously associate and preserve a VEGF polypeptide binding potential.
Figure 3:
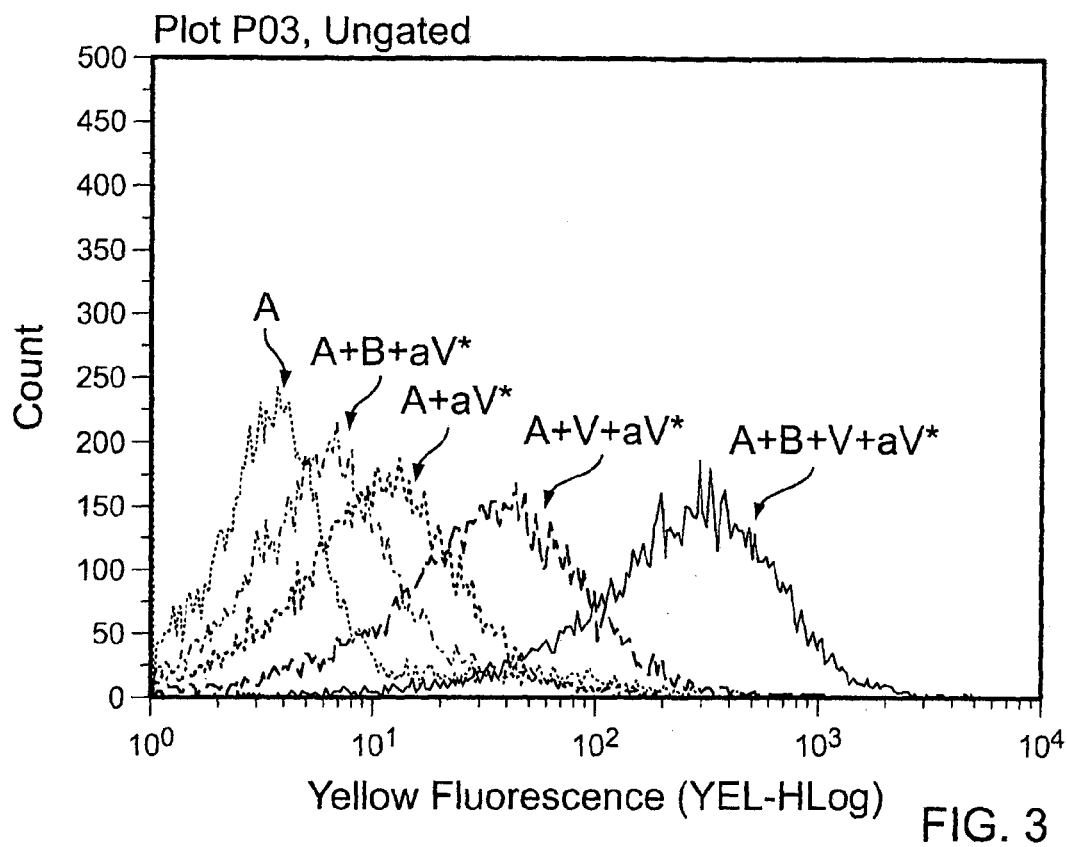
FIG. 3 is graph that contains the flow cytometry data from FIG. 2.
Figure 4:
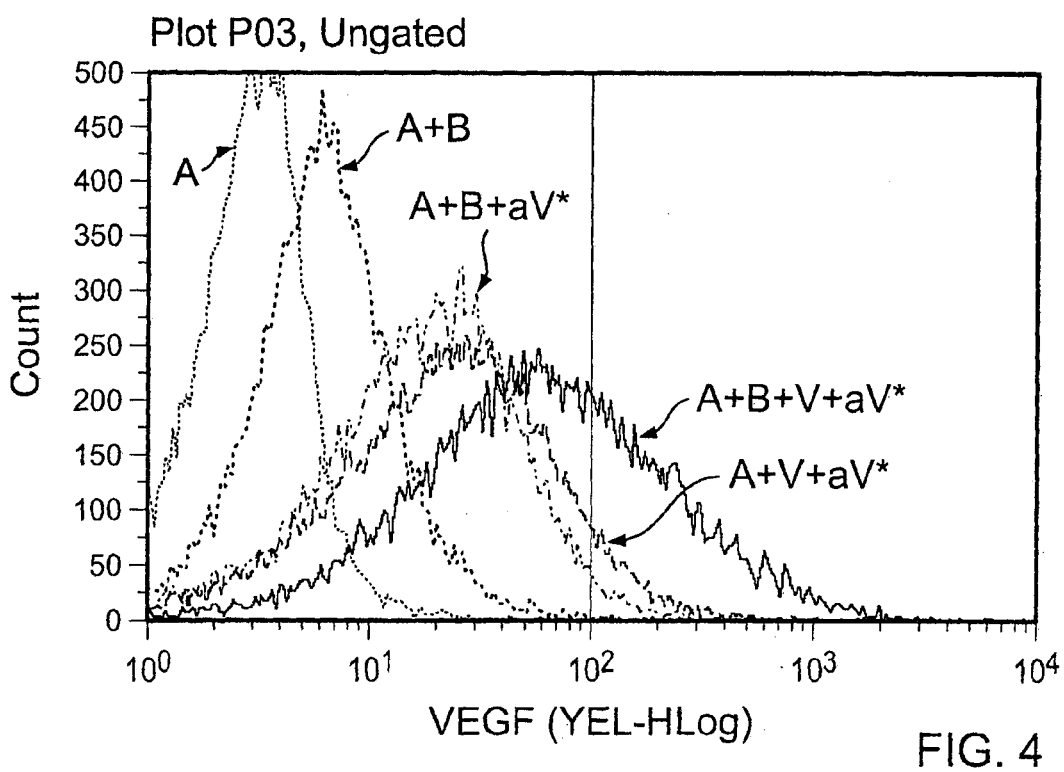
FIG. 4 is a repeat of the experiment of FIG. 3, comparing A alone, A plus aV*, A plus B plus aV*, A plus V plus aV*, or A plus B plus V plus aV*. One difference is in FIG. 3, 500 ng of VEGF was used.
Figure 5:
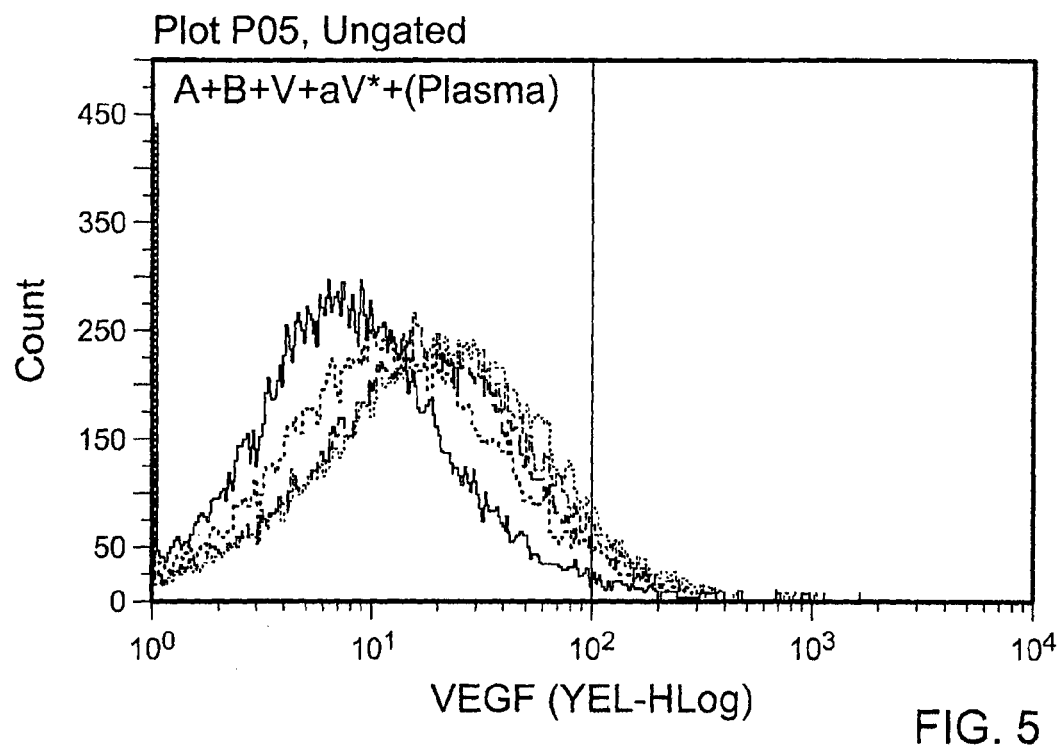
FIG. 5 is a graph plotting flow cytometry data of A plus B incubated in the presence of various concentrations of human plasma (1:1 to 1:16) followed by addition of V and aV*. These results indicate that human plasma diluted in a range of relative volumes (1:1 to 1:16) successfully inhibited the formation of the A+B complex relative to controls.
Figure 6:
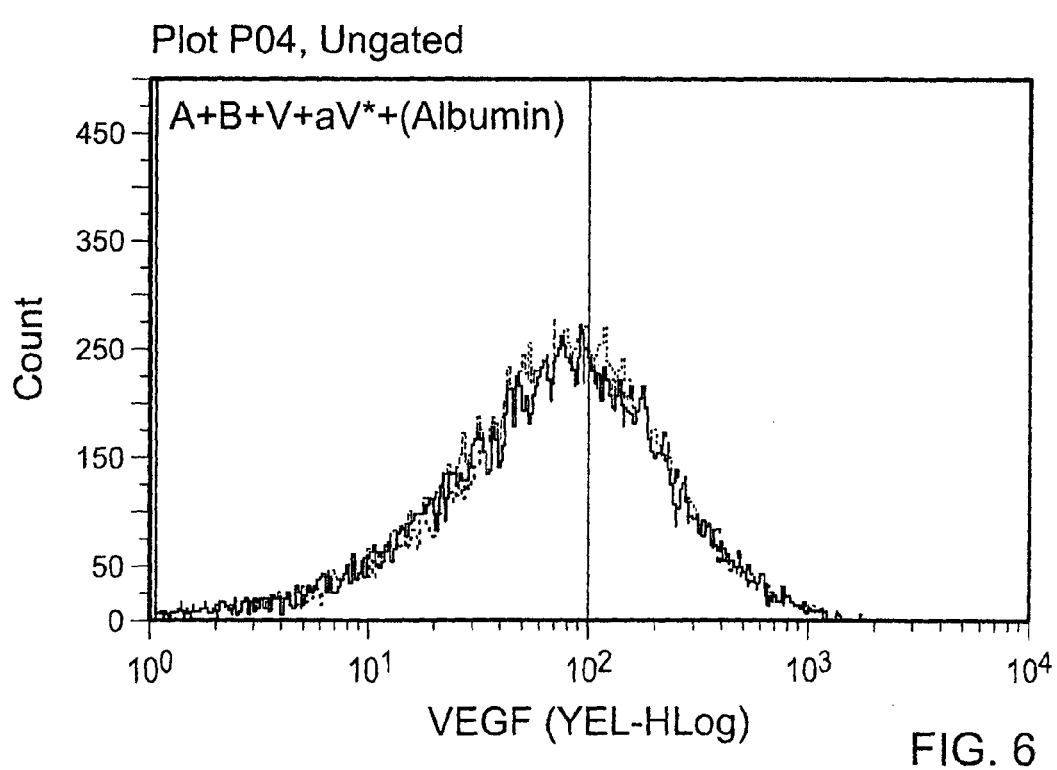
FIG. 6 is a graph plotting flow cytometry data of A plus B incubated in the presence of various concentrations of human serum albumin (500 µg, 50 µg, 5 µg, 0.5 µg, and 0.05 µg/mL) followed by addition of V and aV*. These results indicate that incubation with serum albumin (concentrations ranging from 500 µg/mL to 0.05 µg/mL) did not affect the complexing of A and B.
Figure 7:
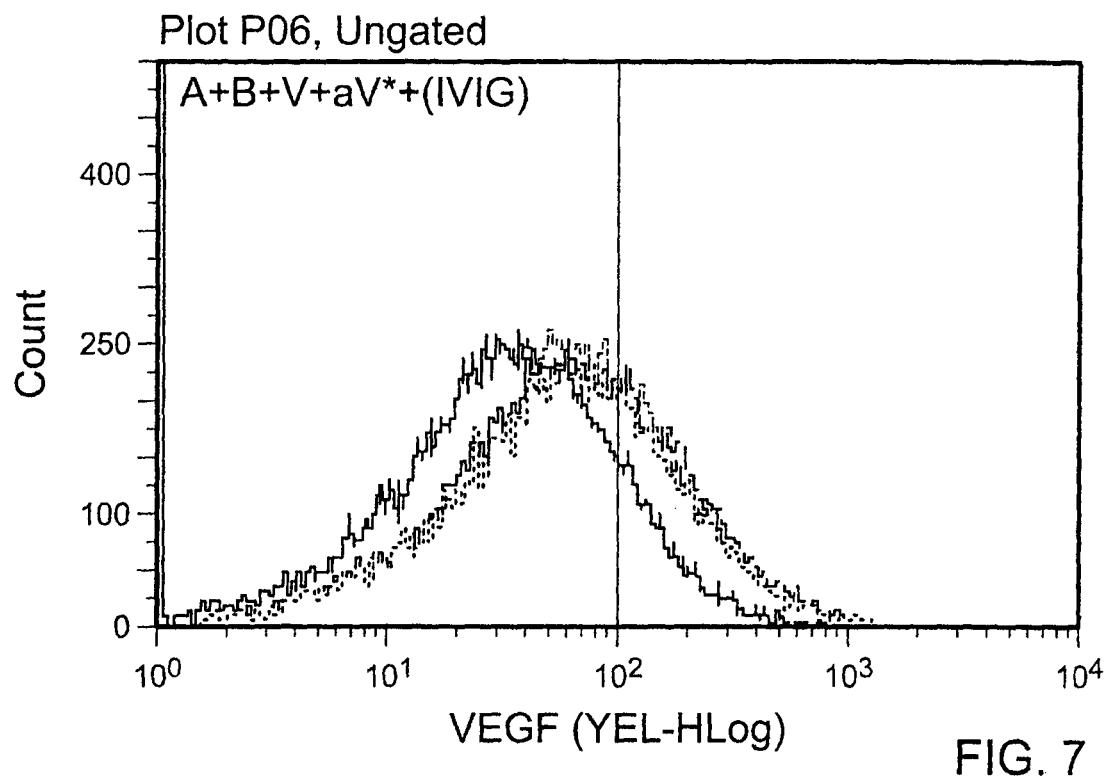
FIG. 7 is a graph plotting flow cytometry data of A plus B incubated in the presence of various concentrations of human polyclonal immunoglobulin (500 µg, 50 µg, 5 µg, 0.5 µg, and 0.05 µg/mL) followed by addition of V and aV*. These results indicate that incubation of A and B with a range of concentrations of human immunoglobulin (IVIG; 500 µg/mL to 0.05 µg/mL) partially inhibited A and B complexing.
Figure 8:
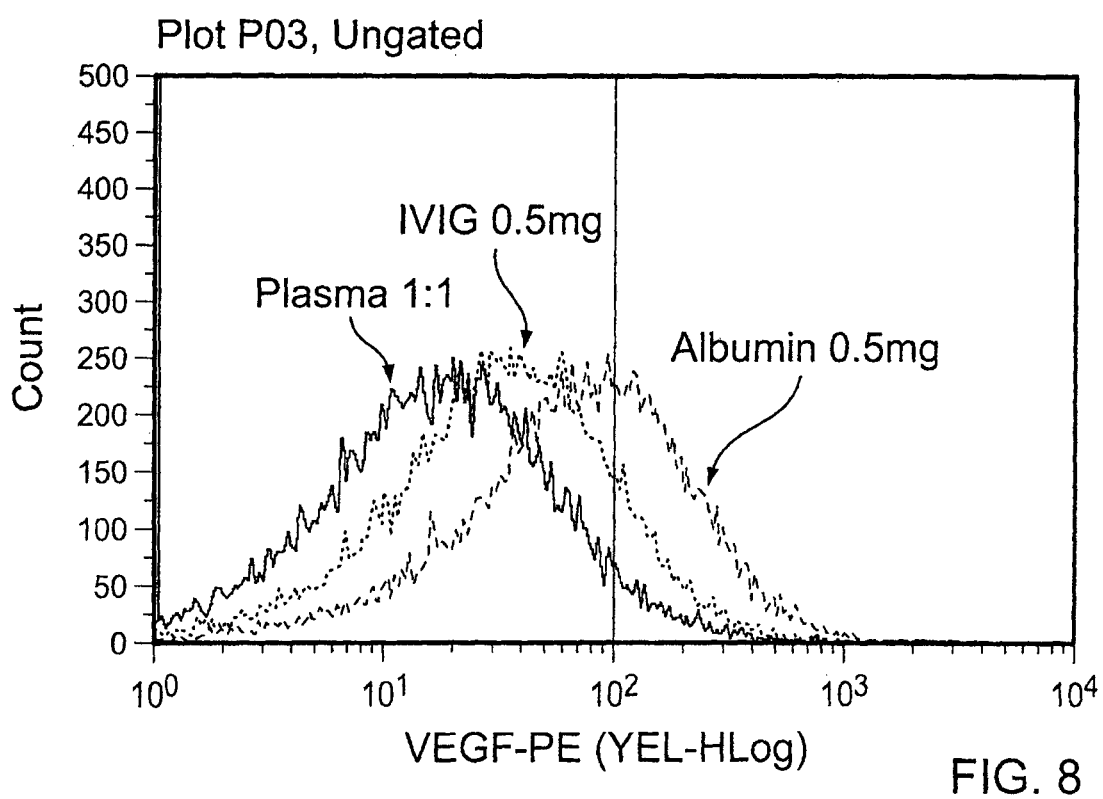
FIG. 8 contain A plus B complexing results in the presence of plasma (1:1), IVIG (0.5 mg/mL), or albumin (0.5 mg/mL). At the highest concentrations of plasma (1:1), IVIG (0.5 mg/mL), or albumin (0.5 mg/mL) tested, the levels of relative inhibition of A plus B complexing differ in diminishing order.

This document provides methods and materials involved in treating cancer (e.g., skin cancers such as melanoma). For example, this document provides methods and materials for using complexes containing albumin-containing nanoparticles (e.g., Abraxane® nanoparticles) and antibodies (e.g., anti-VEGF polypeptide antibodies such as Avastin®) to treat cancer.

The methods and materials provided herein can be used to treat any type of cancer. For example, the methods and materials provided herein can be used to treat skin cancer (e.g., melanoma) and breast cancer. In some cases, the methods and materials provided herein can be used to treat cancer (e.g., skin cancer) in any type of mammal including, without limitation, mice, rats, dogs, cats, horses, cows, pigs, monkeys, and humans. When treating skin cancer, any type of skin cancer, such as melanoma, can be treated using the methods and materials provided herein. For example, stage I, stage II, stage III, or stage IV melanoma can be treated. In some cases, a lymph node positive, a lymph node negative, or a metastatic melanoma can be treated as described herein.

In some cases, complexes containing albumin-containing nanoparticles (e.g., Abraxane® nanoparticles) and antibodies (e.g., anti-VEGF polypeptide antibodies such as Avastin®) can be designed to have an average diameter that is greater than 1 µm. For example, appropriate concentrations of albumin-containing nanoparticles and antibodies can be used such that complexes having an average diameter that is greater than 1 µm are formed. In some cases, manipulations such as centrifugation can be used to form preparations of albumin-containing nanoparticle/antibody complexes where the average diameter of those complexes is greater than 1 µm. In some cases, the preparations of albumin-containing nanoparticle/antibody complexes provided herein can have an average diameter that is between 1 µm and 5 µm (e.g., between 1.1 µm and 5 µm, between 1.5 µm and 5 µm, between 2 µm and 5 µm, between 2.5 µm and 5 µm, between 3 µm and 5 µm, between 3.5 µm and 5 µm, between 4 µm and 5 µm, between 4.5 µm and 5 µm, between 1.1 µm and 4.5 µm, between 1.1 µm and 4 µm, between 1.1 µm and 3.5 µm, between 1.1 µm and 3 µm, between 1.1 µm and 2.5 µm, between 1.1 µm and 2 µm, or between 1.1 µm and 1.5 µm). Preparations of albumin-containing nanoparticle/antibody complexes provided herein having an average diameter that is between 1 µm and 5 µm can be administered systemically (e.g., intravenously) to treat cancers located within a mammal's body. In some cases, the preparations of albumin-containing nanoparticle/antibody complexes provided herein can have an average diameter that is between 5 µm and 50 µm (e.g., between 6 µm and 50 µm, between 7 µm and 50 µm, between 10 µm and 50 µm, between 15 µm and 50 µm, between 20 µm and 50 µm, between 25 µm and 50 µm, between 30 µm and 50 µm, between 35 µm and 50 µm, between 5 µm and 45 µm, between 5 µm and 40 µm, between 5 µm and 35 µm, between 5 µm and 30 µm, between 5 µm and 25 µm, between 5 µm and 20 µm, between 5 µm and 15 µm, or between 10 µm and 30 µm). Preparations of albumin-containing nanoparticle/antibody complexes provided herein having an average diameter that is between 5 µm and 50 µm can be administered into a tumor (e.g., intratumorally) or in a region of a tumor located within a mammal's body.

In some cases, a preparation of albumin-containing nanoparticle/antibody complexes provided herein can have greater than 60 percent (e.g., greater than 65, 70, 75, 80, 90, 95, or 99 percent) of the complexes having a diameter that is between 1 µm and 5 µm (e.g., between 1.1 µm and 5 µm, between 1.5 µm and 5 µm, between 2 µm and 5 µm, between 2.5 µm and 5 µm, between 3 µm and 5 µm, between 3.5 µm and 5 µm, between 4 µm and 5 µm, between 4.5 µm and 5 µm, between 1.1 µm and 4.5 µm, between 1.1 µm and 4 µm, between 1.1 µm and 3.5 µm, between 1.1 µm and 3 µm, between 1.1 µm and 2.5 µm, between 1.1 µm and 2 µm, or between 1.1 µm and 1.5 µm). Preparation of albumin-containing nanoparticle/antibody complexes provided herein having greater than 60 percent (e.g., greater than 65, 70, 75, 80, 90, 95, or 99 percent) of the complexes with a diameter that is between 1 µm and 5 µm can be administered systemically (e.g., intravenously) to treat cancers located within a mammal's body. In some cases, a preparation of albumin-containing nanoparticle/antibody complexes provided herein can have greater than 60 percent (e.g., greater than 65, 70, 75, 80, 90, 95, or 99 percent) of the complexes having a diameter that is between 5 µm and 50 µm (e.g., between 6 µm and 50 µm, between 7 µm and 50 µm, between 10 µm and 50 µm, between 15 µm and 50 µm, between 20 µm and 50 µm, between 25 µm and 50 µm, between 30 µm and 50 µm, between 35 µm and 50 µm, between 5 µm and 45 µm, between 5 µm and 40 µm, between 5 µm and 35 µm, between 5 µm and 30 µm, between 5 µm and 25 µm, between 5 µm and 20 µm, between 5 µm and 15 µm, or between 10 µm and 30 µm). Preparation of albumin-containing nanoparticle/antibody complexes provided herein having greater than 60 percent (e.g., greater than 65, 70, 75, 80, 90, 95, or 99 percent) of the complexes with a diameter that is between 5 µm and 50 µm can be administered into a tumor (e.g., intratumorally) or in a region of a tumor located within a mammal's body.

In general, albumin-containing nanoparticles such as Abraxane® can be contacted with an antibody such as an anti-VEGF polypeptide antibody (e.g., Avastin®) prior to administration to a human to form an albumin-containing nanoparticle/antibody complex (e.g., an Abraxane®/anti-VEGF polypeptide antibody complex). Any appropriate albumin-containing nanoparticle preparation and any appropriate antibody can be used as described herein. For example, Abraxane® nanoparticles can be used as described herein. Examples of antibodies that can be used to form albumin-containing nanoparticle/antibody complexes as described herein include, without limitation, bevacizumab (Avastin®), trastuzumab, and rituxan. For example, an appropriate dose of Abraxane® and an appropriate dose of Avastin® can be mixed together in the same container. This mixture can be incubated at an appropriate temperature (e.g., room temperature, between 15° C. and 30° C., between 15° C. and 25° C., between 20° C. and 30° C., or between 20° C. and 25° C.) for a period of time (e.g., about 30 minutes, or between about 5 minutes and about 60 minutes, between about 5 minutes and about 45 minutes, between about 15 minutes and about 60 minutes, between about 15 minutes and about 45 minutes, between about 20 minutes and about 400 minutes, or between about 25 minutes and about 35 minutes) before being administered to a cancer patient (e.g., a melanoma patient). In some cases, Abraxane® can be contacted with an anti-VEGF polypeptide antibody by injecting both Abraxane® and the anti-VEGF polypeptide antibody either individually or as a pre-mixed combination into an IV bag containing an IV bag solution. The contents of the IV bag including Abraxane®/anti-VEGF polypeptide antibody complexes can be introduced into the patient to be treated.

In some cases, albumin-containing nanoparticles such as Abraxane® can be contacted with an antibody such as an anti-VEGF polypeptide antibody (e.g., Avastin) to form albumin-containing nanoparticle/antibody complexes (e.g., Abraxane®/anti-VEGF polypeptide antibody complexes) that are stored prior to being administered to a cancer patient (e.g., a melanoma patient). For example, a composition containing albumin-containing nanoparticle/antibody complexes can be formed as described herein and stored for a period of time (e.g., days or weeks) prior to being administered to a cancer patient.

Any appropriate method can be used to obtain albumin-containing nanoparticles such as Abraxane® and an antibody such as an anti-VEGF polypeptide antibody. For example, Abraxane® can be obtained from Celgene Corp. or as described elsewhere (U.S. Pat. No. 6,537,579). Avastin® can be obtained from Genentech Corp. or Roche Corp. or as described elsewhere (U.S. Pat. No. 6,054,297).

In some cases, the combination of an albumin-containing nanoparticle such as Abraxane® and an antibody such as anti-VEGF polypeptide antibody can include one or more other agents such as an alkylating agent (e.g., a platinum compound). Examples of platinum compounds that can be used as an alkylating agent include, without limitation, carboplatin (Paraplatin®), cisplatin (Platinol®), oxaliplatin (Eloxatin®), and BBR3464. Examples of other agents that can be included within an albumin-containing nanoparticle/antibody complex provided herein include, without limitation, bendamustine, bortezomib, cabazitaxel, chlorambucil, dasatinib, docetaxel, doxorubicin, epirubicin, erlotinib, etoposide, everolimus, gefitinib, idarubicin, hydroxyurea, imatinib, lapatinib, melphalan, mitoxantrone, nilotinib, oxaliplatin, pazopanib, pemetrexed, romidepsin, sorafenib, sunitinib, teniposide, vinblastine, and vinorelbine.

Any appropriate method can be used to administer an albumin-containing nanoparticle/antibody complex provided herein (e.g., Abraxane®/anti-VEGF polypeptide antibody complexes) to a mammal. For example, a composition containing albumin-containing nanoparticle/antibody complexes such as Abraxane®/anti-VEGF polypeptide antibody complexes can be administered via injection (e.g., subcutaneous injection, intramuscular injection, intravenous injection, or intrathecal injection).

Before administering a composition containing an albumin-containing nanoparticle/antibody complex provided herein (e.g., Abraxane®/anti-VEGF polypeptide antibody complexes) to a mammal, the mammal can be assessed to determine whether or not the mammal has cancer (e.g., skin cancer). Any appropriate method can be used to determine whether or not a mammal has cancer (e.g., skin cancer). For example, a mammal (e.g., human) can be identified as having skin cancer using standard diagnostic techniques. In some cases, a tissue biopsy can be collected and analyzed to determine whether or not a mammal has skin cancer.

After identifying a mammal as having cancer (e.g., skin cancer), the mammal can be administered a composition containing albumin-containing nanoparticle/antibody complexes provided herein (e.g., Abraxane®/anti-VEGF polypeptide antibody complexes). For example, a composition containing Abraxane®/anti-VEGF polypeptide antibody complexes can be administered prior to or in lieu of surgical resection of a tumor. In some cases, a composition containing albumin-containing nanoparticle/antibody complexes provided herein (e.g., Abraxane®/anti-VEGF polypeptide antibody complexes) can be administered following resection of a tumor.

A composition containing albumin-containing nanoparticle/antibody complexes provided herein (e.g., Abraxane®/anti-VEGF polypeptide antibody complexes) can be administered to a mammal in any appropriate amount, at any appropriate frequency, and for any appropriate duration effective to achieve a desired outcome (e.g., to increase progression-free survival). In some cases, a composition containing albumin-containing nanoparticle/antibody complexes provided herein (e.g., Abraxane®/anti-VEGF polypeptide antibody complexes) can be administered to a mammal having cancer (e.g., skin cancer) to reduce the progression rate of the cancer (e.g., melanoma) by 5, 10, 25, 50, 75, 100, or more percent. For example, the progression rate can be reduced such that no additional cancer progression is detected. Any appropriate method can be used to determine whether or not the progression rate of cancer (e.g., skin cancer) is reduced. For example, the progression rate of skin cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer (e.g., skin cancer) after treatment can be determined and compared to the stage before treatment to determine whether or not the progression rate was reduced.

In some cases, a composition containing albumin-containing nanoparticle/antibody complexes provided herein (e.g., Abraxane®/anti-VEGF polypeptide antibody complexes) can be administered to a mammal having cancer (e.g., skin cancer) under conditions where progression-free survival is increased (e.g., by 5, 10, 25, 50, 75, 100, or more percent) as compared to the median progression-free survival of corresponding mammals having untreated cancer (e.g., untreated skin cancer) or the median progression-free survival of corresponding mammals having cancer (e.g., skin cancer) treated with Abraxane® and an antibody (e.g., an anti-VEGF polypeptide antibody) without forming Abraxane®/antibody complexes (e.g., without forming Abraxane®/anti-VEGF polypeptide antibody complexes). In some cases, a composition containing albumin-containing nanoparticle/antibody complexes provided herein (e.g., Abraxane®/anti-VEGF polypeptide antibody complexes) can be administered to a mammal having cancer (e.g., skin cancer) to increase progression-free survival by 5, 10, 25, 50, 75, 100, or more percent as compared to the median progression-free survival of corresponding mammals having cancer (e.g., skin cancer) and having received Abraxane® or an antibody (e.g., an anti-VEGF polypeptide antibody) alone. Progression-free survival can be measured over any length of time (e.g., one month, two months, three months, four months, five months, six months, or longer).

In some cases, a composition containing albumin-containing nanoparticle/antibody complexes provided herein (e.g., Abraxane®/anti-VEGF polypeptide antibody complexes) can be administered to a mammal having cancer (e.g., skin cancer) under conditions where the 8-week progression-free survival rate for a population of mammals is 65% or greater (e.g., 66%, 67%, 68%, 69%, 70%, 71%, 72%, 73%, 74%, 75%, 76%, 77%, 78%, 79%, 80% or greater) than that observed in a population of comparable mammals not receiving a composition containing albumin-containing nanoparticle/antibody complexes provided herein (e.g., Abraxane®/anti-VEGF polypeptide antibody complexes). In some cases, a composition containing albumin-containing nanoparticle/antibody complexes provided herein (e.g., Abraxane®/anti-VEGF polypeptide antibody complexes) can be administered to a mammal having cancer (e.g., skin cancer) under conditions where the median time to progression for a population of mammals is at least 150 days (e.g., at least 155, 160, 163, 165, or 170 days).

An effective amount of a composition containing albumin-containing nanoparticle/antibody complexes provided herein (e.g., Abraxane®/anti-VEGF polypeptide antibody complexes) can be any amount that reduces the progression rate of cancer (e.g., skin cancer), increases the progression-free survival rate, or increases the median time to progression without producing significant toxicity to the mammal. Typically, an effective amount of Abraxane® can be from about 50 mg/m$^2$ to about 150 mg/m$^2$ (e.g., about 80 mg/m$^2$), and an effective amount of an anti-VEGF polypeptide antibody such as bevacizumab can be from about 5 mg/kg to about 20 mg/kg (e.g., about 10 mg/kg). If a particular mammal fails to respond to a particular amount, then the amount of Abraxane® or anti-VEGF polypeptide antibody can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer (e.g., skin cancer) may require an increase or decrease in the actual effective amount administered.

The frequency of administration can be any frequency that reduces the progression rate of cancer (e.g., skin cancer), increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. A course of treatment with a composition containing Abraxane®/anti-VEGF polypeptide antibody complexes can include rest periods. For example, a composition containing Abraxane®/anti-VEGF polypeptide antibody complexes can be administered over a two week period followed by a two week rest period, and such a regimen can be repeated multiple times.

As with the effective amount, various factors can influence the actual frequency of administration used for a particular application. For example, the effective amount, duration of treatment, use of multiple treatment agents, route of administration, and severity of the skin cancer may require an increase or decrease in administration frequency.

An effective duration for administering a composition provided herein can be any duration that reduces the progression rate of cancer (e.g., skin cancer), increases the progression-free survival rate, or increases the median time to progression without producing significant toxicity to the mammal. Thus, the effective duration can vary from several days to several weeks, months, or years. In general, the effective duration for the treatment of skin cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer (e.g., skin cancer).

A composition containing albumin-containing nanoparticle/antibody complexes provided herein (e.g., Abraxane®/anti-VEGF polypeptide antibody complexes) can be in any appropriate form. For example, a composition provided herein can be in the form of a solution or powder with or without a diluent to make an injectable suspension. A composition also can contain additional ingredients including, without limitation, pharmaceutically acceptable vehicles. A pharmaceutically acceptable vehicle can be, for example, saline, water, lactic acid, mannitol, or combinations thereof.

After administering a composition provided herein to a mammal, the mammal can be monitored to determine whether or not the cancer (e.g., skin cancer) was treated. For example, a mammal can be assessed after treatment to determine whether or not the progression rate of melanoma was reduced (e.g., stopped). As described herein, any method can be used to assess progression and survival rates.

In some cases, nanoparticles containing albumin (e.g., nanoparticles with an albumin shell) and an agent other than placitaxel can be used as described herein in place of or in combination with Abraxane®. For example, albumin-containing nanoparticles designed to carry a cancer chemotherapeutic agent can be used to form nanoparticle/anti-VEGF polypeptide antibody complexes that can be used as described herein. An example of such a cancer chemotherapeutic agent includes, without limitation, vinblastine.

The invention will be further described in the following examples, which do not limit the scope of the invention described in the claims.

EXAMPLES

Example 1

Contacting Abraxane® with Avastin® Results in the Formation of Abraxane®/Avastin® complexes Abraxane® (1 mg/mL) and Avastin (25 mg/mL) were stored at 4° C. 10 µg (10 µL) of Abraxane® nanoparticles and 500 µg (20 µL) of Avastin were mixed in a total volume of 30 µL. The Abraxane® and Avastin were incubated at room temperature for 30 minutes.

After incubation, the Abraxane® nanoparticles were spun and washed three times with 1× PBS to eliminate unbound bevacizumab. The nanoparticles were spun at 5000 rpm for 5 minutes and resuspended in 50 µL of 1× PBS.

100 ng or 500 ng of VEGF was added to each tube for 30 minutes at room temperature, and the washes were repeated to eliminate unbound VEGF. PE anti-human VEGF was added at a 1:50 dilution, and the particles were once again incubated and washed. Visualization was done by flow cytometry, and percentage of PE (VEGF) positive particles was determined (FIGS. 1-4). Various combinations of agents were tested as indicated in the figures. These results demonstrate that Abraxane® and bevacizumab spontaneously associate in a manner that preserves VEGF binding potential.

Figure 9:
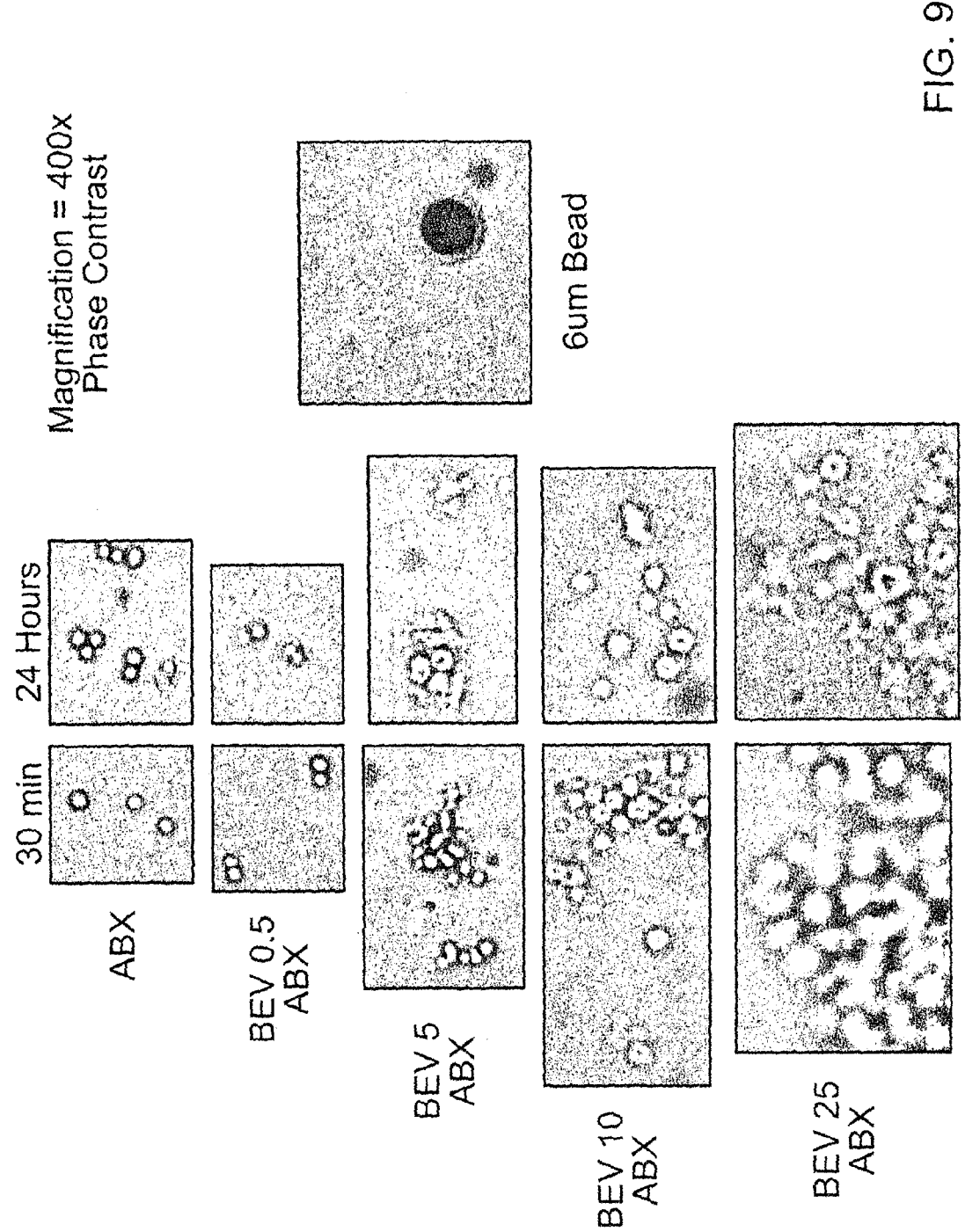
FIG. 9 contains photographs of light microscope images of Abraxane® (ABX) or mixtures of Abraxane® (ABX) and bevacizumab (BEV; 0.5, 5, 10, or 25 mg/mL) either 4 or 24 hours after mixing.

Abraxane® nanoparticles were mixed with varying concentrations of bevacizumab (0.5, 5, 10, and 25 mg/mL). The particles were viewed by light microscopy at 4 and 24 hours after mixing. The macromolecular size of the ABX:BEV complexes was dependent on the concentration of the bevacizumab added and the Abraxane® nanoparticles (FIG. 9). Once a maximum size was reached, the ABX:BEV complexes began to break down within about 24 hours (FIG. 9).

Figure 10:
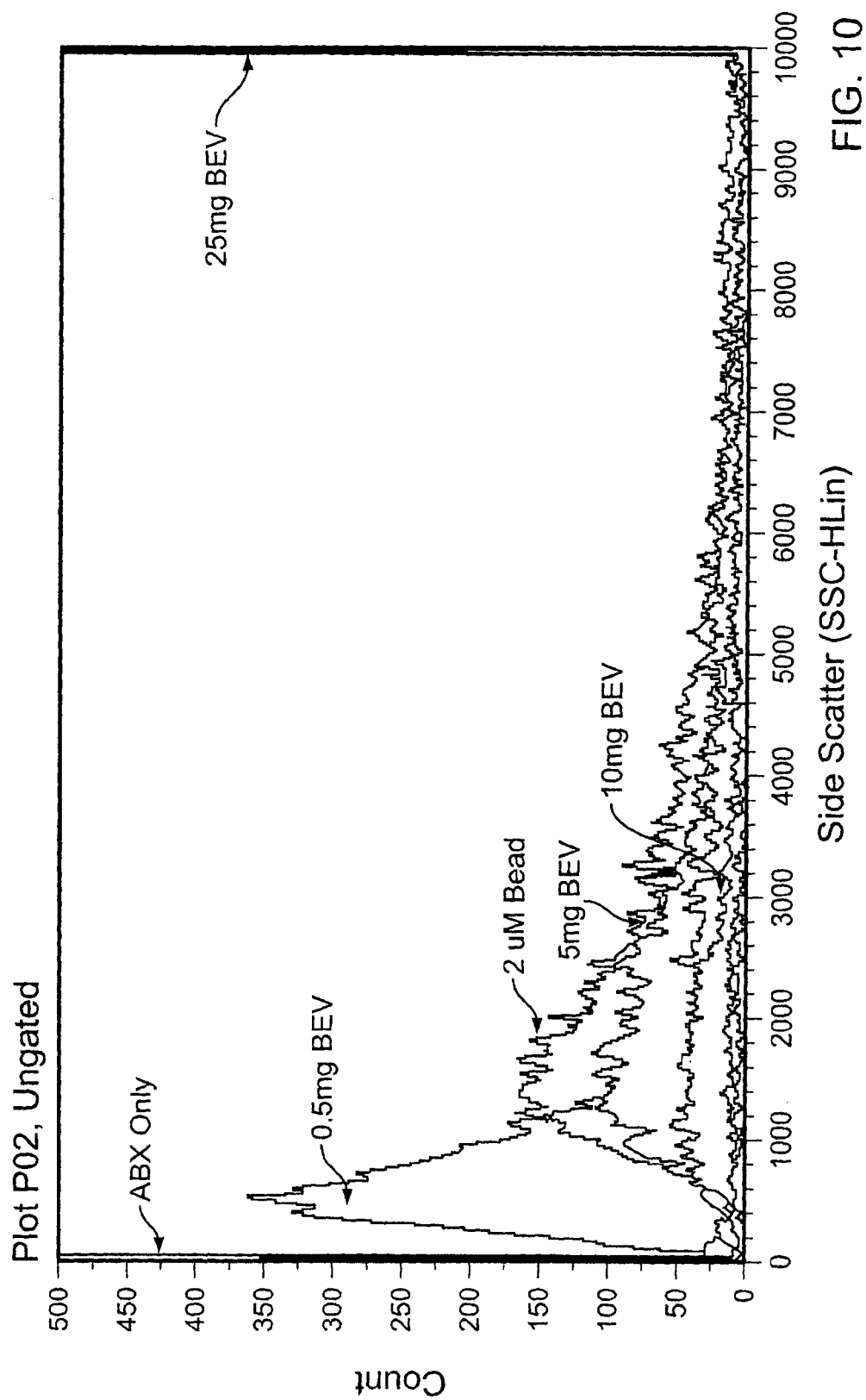
FIG. 10 is a graph plotting flow cytometry results of Abraxane® alone, ABX:BEV complexes, and 2 µm standard beads.

Bevacizumab was added to Abraxane® nanoparticles in varying concentrations (0.5, 5, 10, 25 mg/mL) and incubated for 30 minutes at room temperature to allow complex formation. Abraxane® nanoparticles alone, ABX:BEV complexes, and 2 µm standard beads were visualized by flow cytometry. The complex size increased with increased concentrations of bevacizumab (FIG. 10). The larger the particle-size, the further to the right the peak will be. These results demonstrate that complex size can be manipulated by varying the concentration of bevacizumab added.

In another study, Abraxane® nanoparticles and bevacizumab were incubated together for 4 hours and overnight at 1 mg/mL or 10 mg/mL. Abraxane® nanoparticles alone were also incubated for 4 hours and overnight as a control. After the allotted time was reached, the complexes were spun down at 7500 RPM for 5 minutes. The supernatants were collected and mixed 1:1 with Laemmli buffer and boiled at 100 degrees for 3 minutes. 20 µL of sample was loaded onto a 7.5% Tris-HCl Criteron gel. A high range molecular weight marker (BioRad) was added for size determination. The gel was run for 3 hours at 75V.

After the gel ran to completion, the gel was placed in a transfer cassette so the proteins could be moved onto a PVDF membrane. The transfer took place overnight at 4° C. running at 20V. The membrane was removed and rocked in TBST containing 5% milk to block for 3 hours at room temperature. The primary antibodies used were Rabbit anti-Taxol (1:500 dilution) and goat anti-mouse IgG-Fab specific-HRP conjugated (1:500 dilution). Antibodies were diluted into 10 mL of TBST with 5% milk. Primary antibodies were allowed to bind overnight at 4° C. while rocking Primary antibodies were removed, and the membranes were washed three times for 10 minutes with TBST. The taxol blot was incubated in a 1:1000 dilution of secondary anti-rabbit IgG-HRP for 1.5 hours rocking at room temperature. The anti-mouse IgG (Bevacizumab) membrane was incubated in ECL detection reagent (GE Amershem) for 5 minutes before it was exposed to film. Membrane was exposed for 10 seconds, 1 minute, and 5 minutes.

After the incubation in secondary antibody, the taxol blot was washed with TBST for 10 minutes three times. The membrane was then placed in ECL detection reagent for 5 minutes and exposed to film. The exposure times were 1 second, 2 seconds, and 10 seconds.

Figure 15:
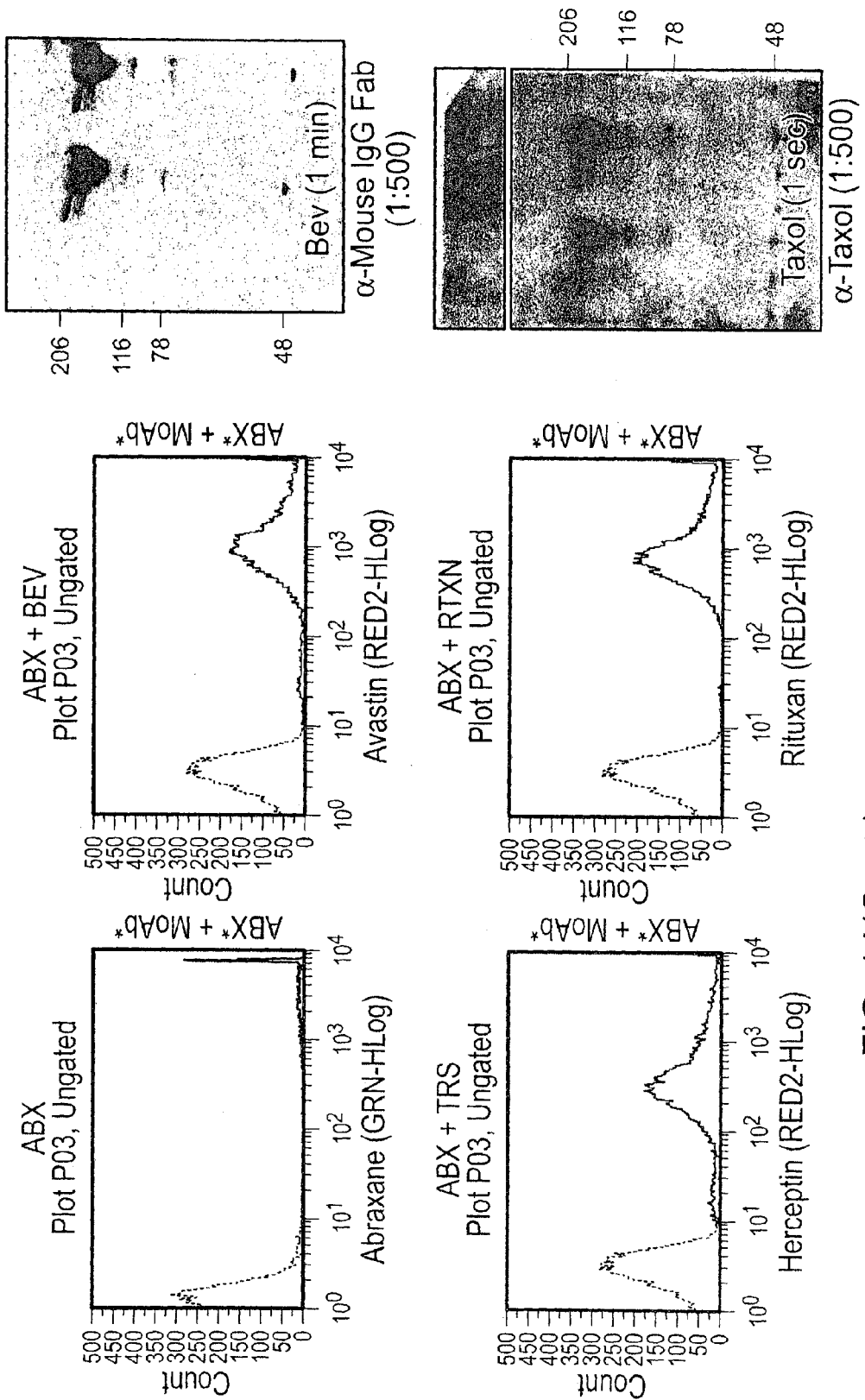
FIG. 15 contains photographs of Western blot analyses of the indicated materials assessed for bevacizumab or taxol.

The IgG blot was specific for the mouse portion of the bevacizumab humanized antibody. A clear concentration dependent increase from complexes mixed at 1 mg/mL to 10 mg/mL was observed (FIG. 15). Taxol is a small molecule around 20 kDa. Free taxol was observed at the bottom of the blot, but it also was observed running at the bevacizumab molecular weight (149 kDa; FIG. 15). These results demonstrate that taxol was bound to the bevacizumab in the supernatant after the large particles were removed by centrifugation.

Figure 16:
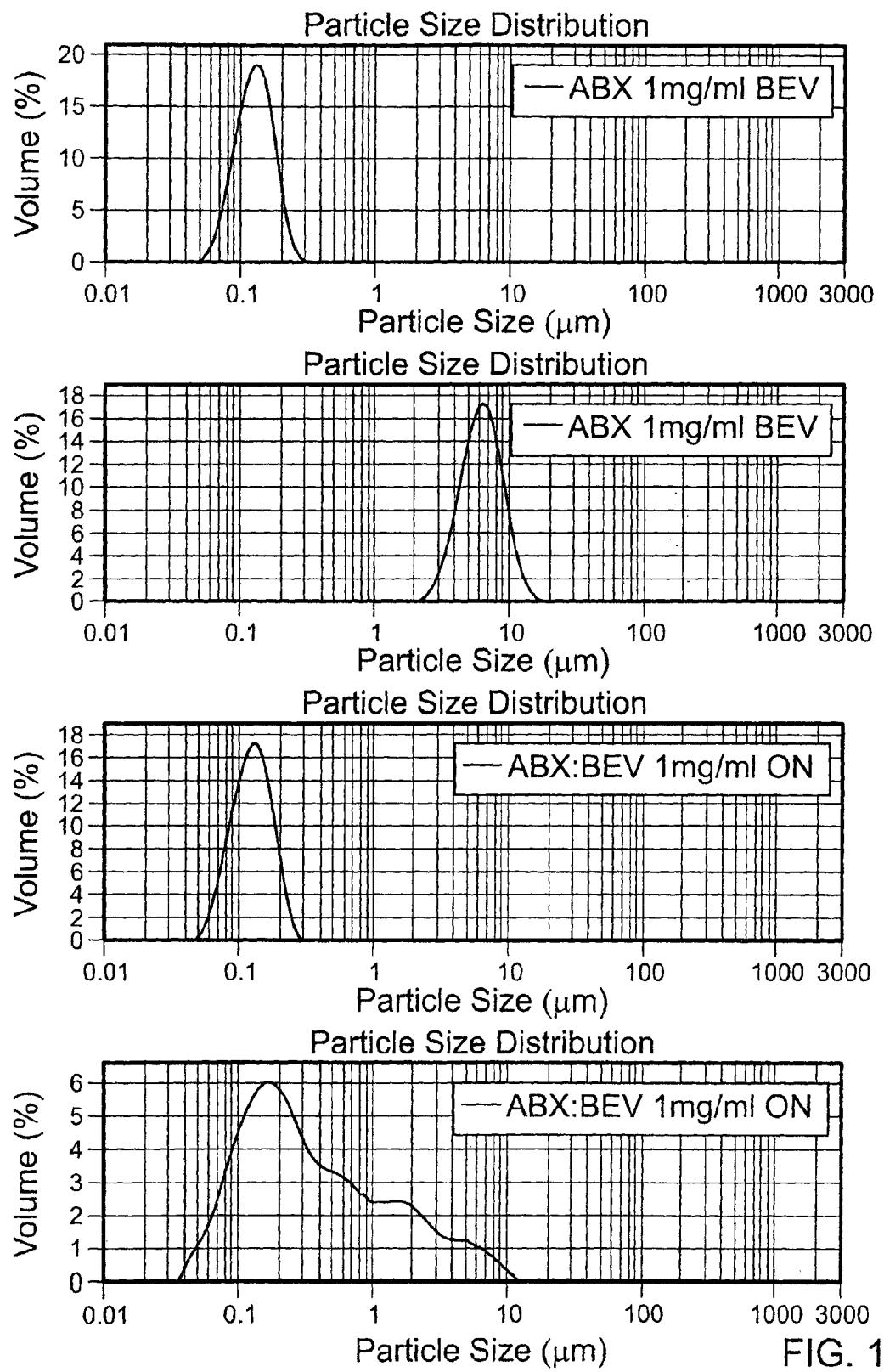
FIG. 16 contains graphs of the size distributions of the indicated complexes incubated for the indicated time.
Figure 17:
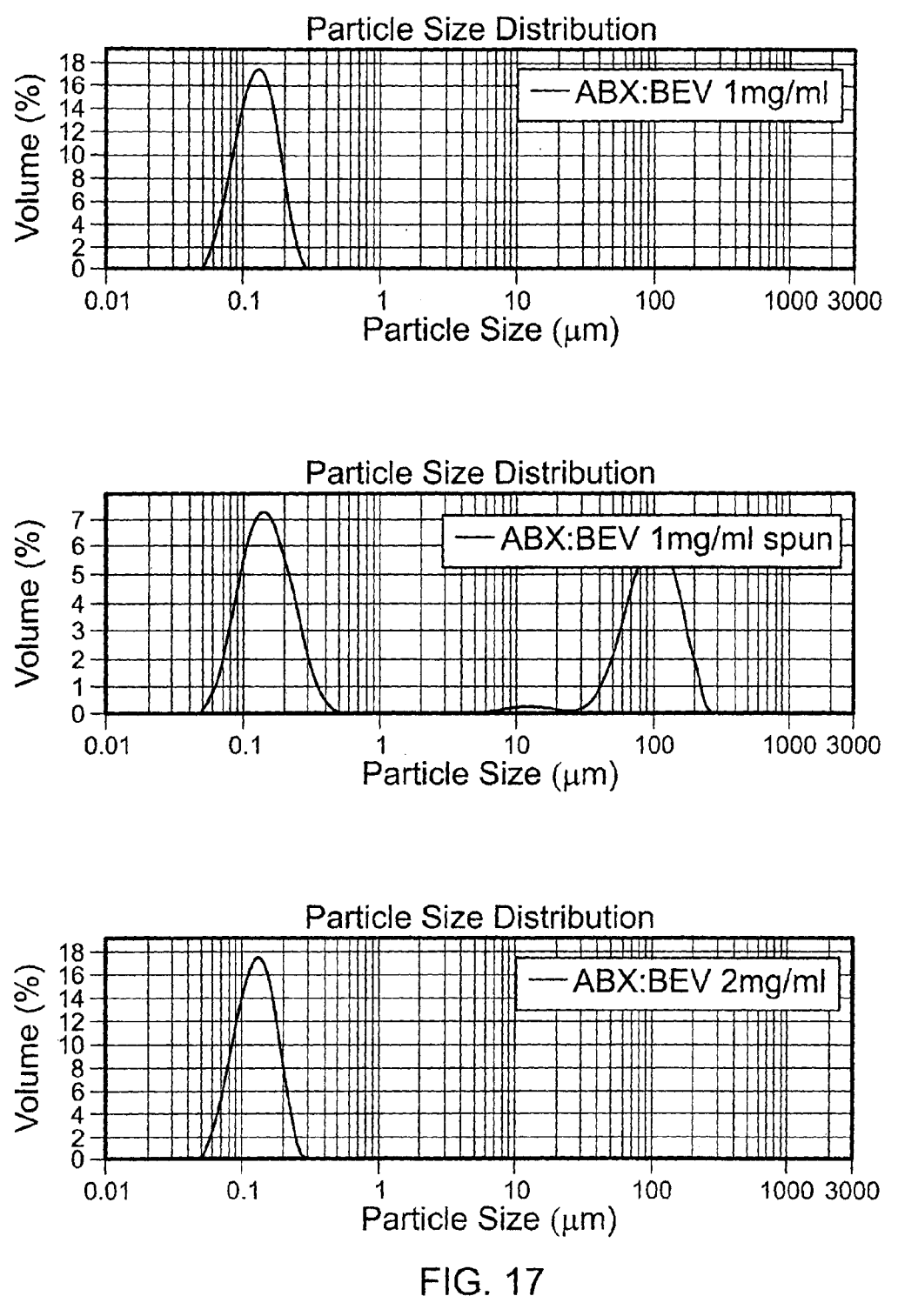
Figure 17:
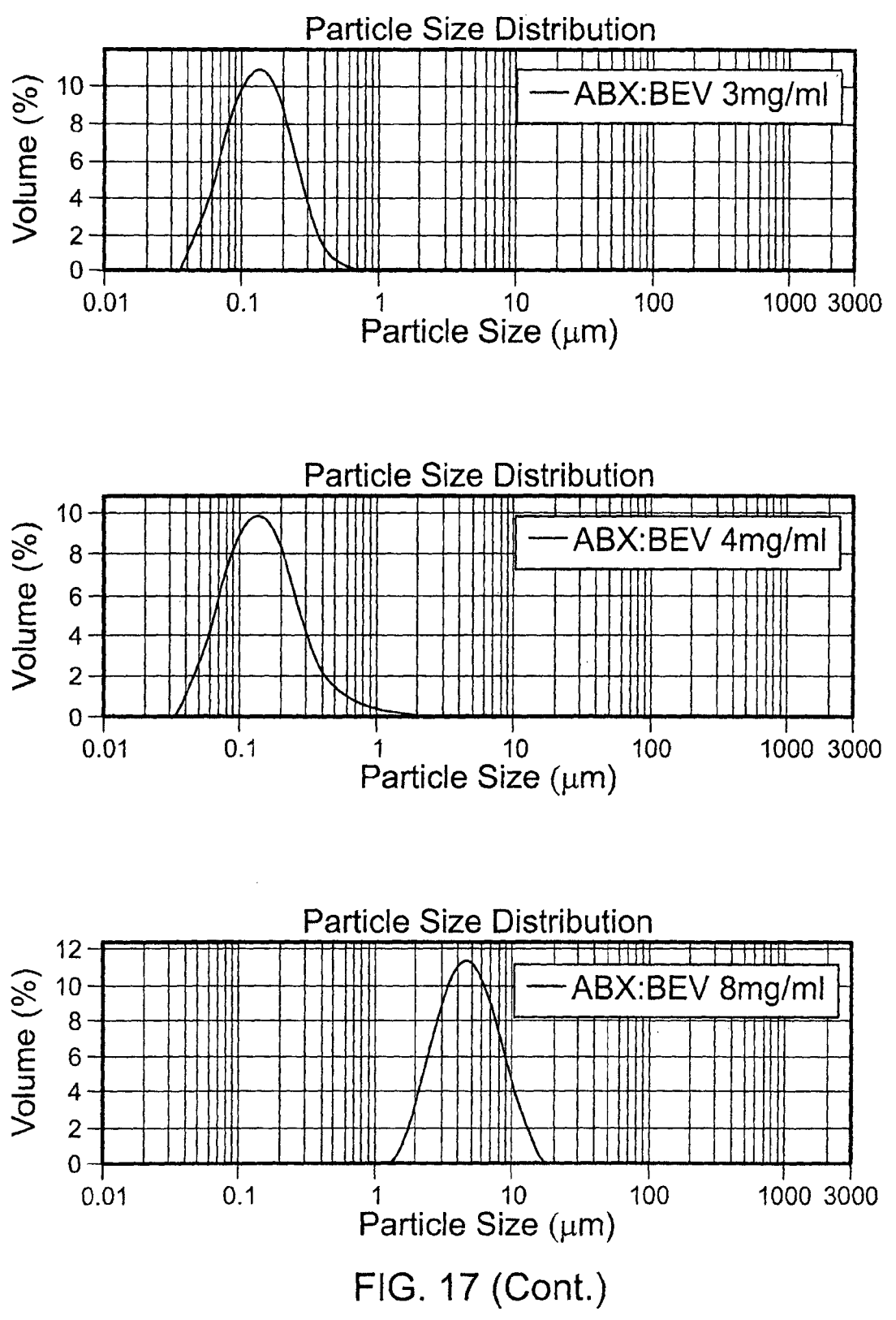

In another study, Abraxane® nanoparticles and bevacizumab were incubated for various times (1, 4, and 12 hours), and the particle size distribution of the resulting complexes was determined relative to Abraxane® nanoparticles alone using the Malvern Mastersizer 2000E. The size of the complexes generated was a function of antibody concentration and incubation time (FIGS. 16 and 17). In FIG. 16, 1 and 10 mg/mL of bevacizumab was incubated with Abraxane® nanoparticles for 4 hours and overnight. The complexes generated with 10 mg/mL bevacizumab were much larger (8.479 µm) than those with 1 mg/mL bevacizumab (0.165 µm). After an overnight incubation, the larger complexes began to break down.

In FIG. 17, complex size increased with concentration of bevacizumab added when incubated for 1 hour at room temperature. In addition, larger complexes were formed when 1 mg/mL bevacizumab was incubated with Abraxane® nanoparticles, spun, and resuspended as compared to the size observed when the same amount (1 mg/mL) of bevacizumab was incubated with Abraxane® nanoparticles without spinning the preparation (FIG. 17). These results demonstrate that complex size can be manipulated by altering concentrations, by manual forces (e.g., centrifugation), or by both.

Figure 20:
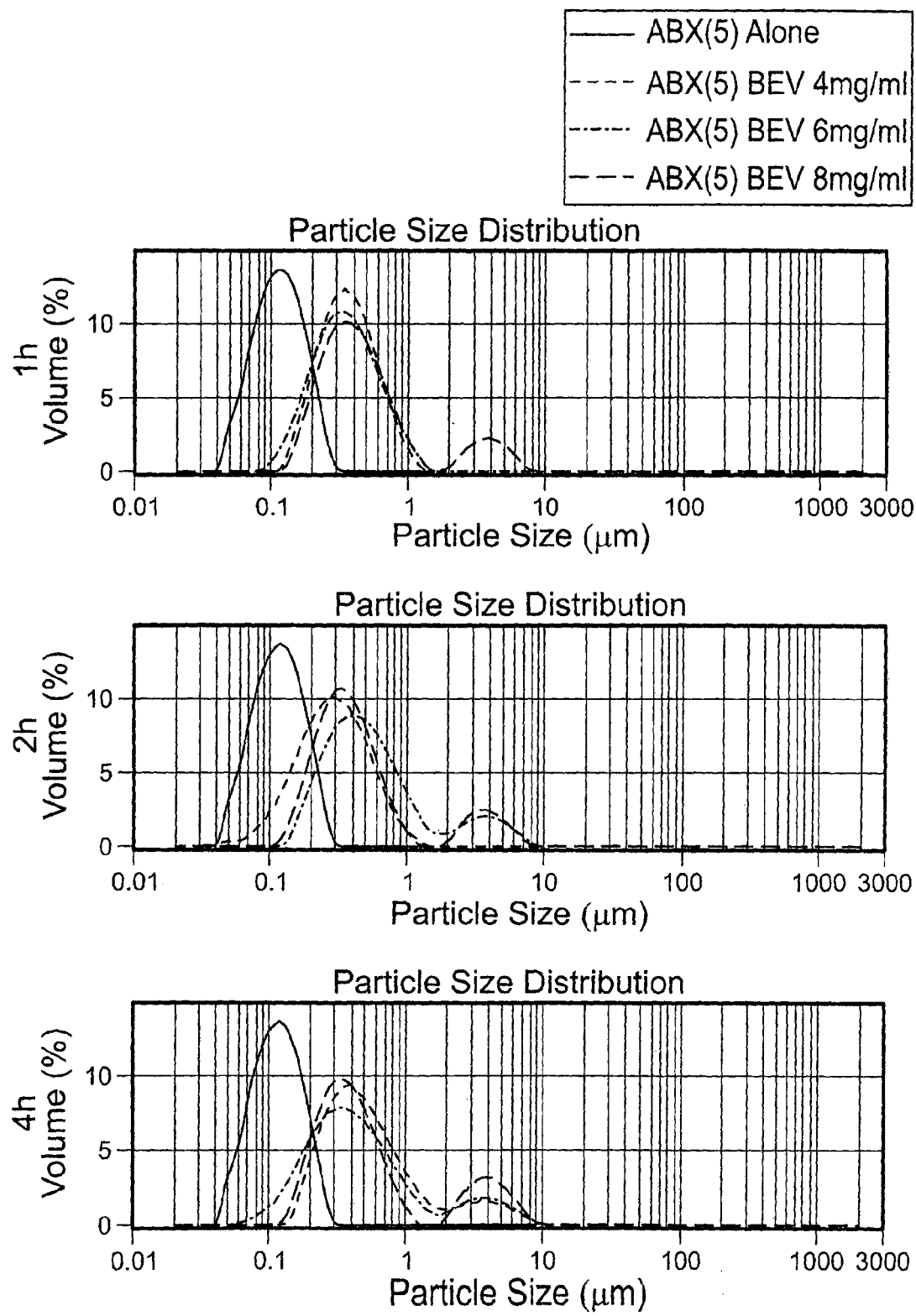
FIG. 20 contains graphs plotting the particle size distribution for ABX:BEV complexes as determined using a Mastersizer 2000E (Malvern Instruments Ltd., Worcestershire, England). ABX (20 mg/mL) and BEV (16, 24, or 32 mg/mL) were incubated for 1, 2, or 4 hours at room temperature. After incubation, the mixtures were diluted 1:4 for a final concentration of ABX (5 mg/mL) and BEV (4, 6, or 8 mg/mL), and the diluted samples analyzed using a Mastersizer 2000E.

In another study, Abraxane® nanoparticles were dissolved at a concentration of 20 mg/mL, and bevacizumab was added at a final concentration of 16, 24, or 32 mg/mL. The mixtures were incubated at room temperature for various times (1, 2, and 4 hours). After this incubation, the mixture was diluted 1:4 (final concentration of Abraxane=5 mg/mL; final concentrations of bevacizumab=4, 6, or 8 mg/mL). The particle size distribution of the resulting complexes was determined relative to Abraxane® nanoparticles alone using the Malvern Mastersizer 2000E. The size of the complexes generated was a function of antibody concentration and incubation time (FIG. 20).

Abraxane and bevacizmab were mixed and incubated for 30 minutes at room temperature to allow complex formation. Mice were injected with 100 µL of the complexes containing 5 mg of Abraxane and 1 mg of bevacizumab in the dorsal tail vein. Injection of the complexes did not harm any mice.

Example 2

Human Plasma Inhibits the Formation of Abraxane®/Avastin® Complexes

10 µL (10 µg) of Abraxane® was added to eppendorf tubes, and 500 µg (25 µL) of avastin was added and resuspended in a final volume of 50 µL. Human plasma was titrated using 1:2 dilutions (1:2, 1:4, 1:8, or 1:16). 50 µL of plasma and 50 µL of each plasma titration were added to the tubes with Abraxane® and avastin. In some cases, human serum albumin (500 µg, 50 µg, 5 µg, 0.5 µg, or 0.05 µg/mL) or human polyclonal immunoglobulin (500 µg, 50 µg, 5 µg, 0.5 µg, and 0.05 µg/mL) was added to the tubes in place of human plasma.

After a 30 minute incubation at room temperature, the Abraxane® nanoparticles were washed in 1× PBS twice. 100 ng of VEGF was added to each tube for 30 minutes at room temperature, and the washes were repeated. PE anti-human VEGF was added at a 1:50 dilution, and particles were once again incubated and washed. Visualization was done by flow cytometry, and percentage of PE (VEGF) positive particles was determined (FIG. 5-8).

Example 3

Figure 11:
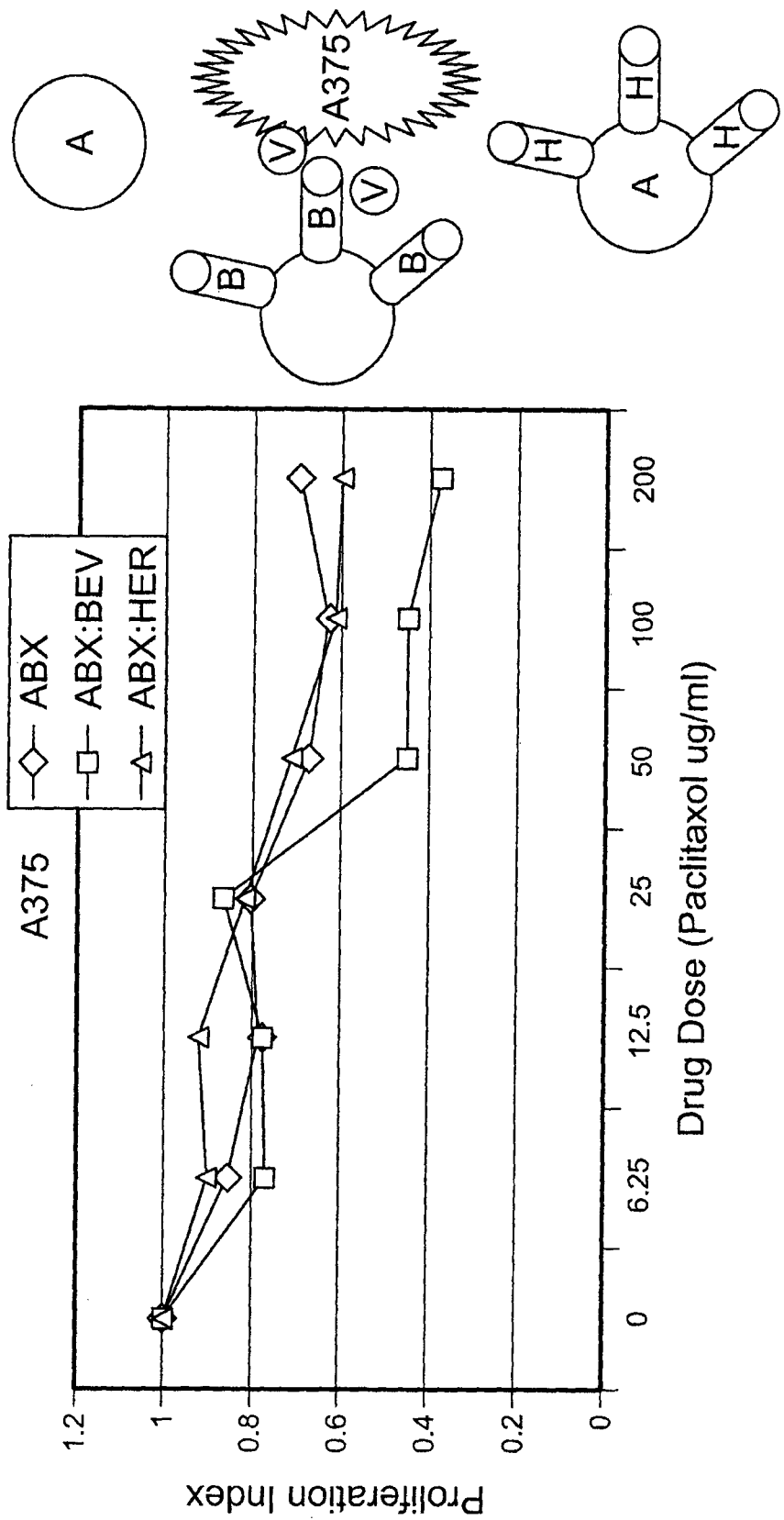
FIG. 11 is graph plotting the proliferation index for A375 cells (a melanoma tumor cell line) exposed to Abraxane® (ABX) only, Abraxane®:Herceptin (non-VEGF targeting) complexes, or Abraxane®:Bevacizumab (VEGF targeting) complexes at the indicated dose.

Abraxane®/Avastin® Complexes have a Higher Level of Cell Toxicity than Abraxane® Alone or Abraxane®/Herceptin Complexes The VEGF producing melanoma tumor cell line, A375, was incubated overnight in the presence of Abraxane® nanoparticles only, Abraxane®/Herceptin (non-VEGF targeting) complexes, and Abraxane®/Avastin® (ABX:BEV; VEGF targeting) complexes. Increasing doses of drug were added to the cells to give 6.25, 12.5, 25, 50, 100, and 200 µg/mL of taxol. After the overnight incubation, cell proliferation was determined by measuring the level of DNA synthesis. A higher level of cell toxicity (less DNA synthesis) of cells incubated with the VEGF targeting complexes (ABX:BEV) relative the ABX alone and non-VEGF targeted complexes (ABX:HER) (FIG. 11).

Example 4

Stability of Abraxane®/Avastin® Complexes

Figure 12:
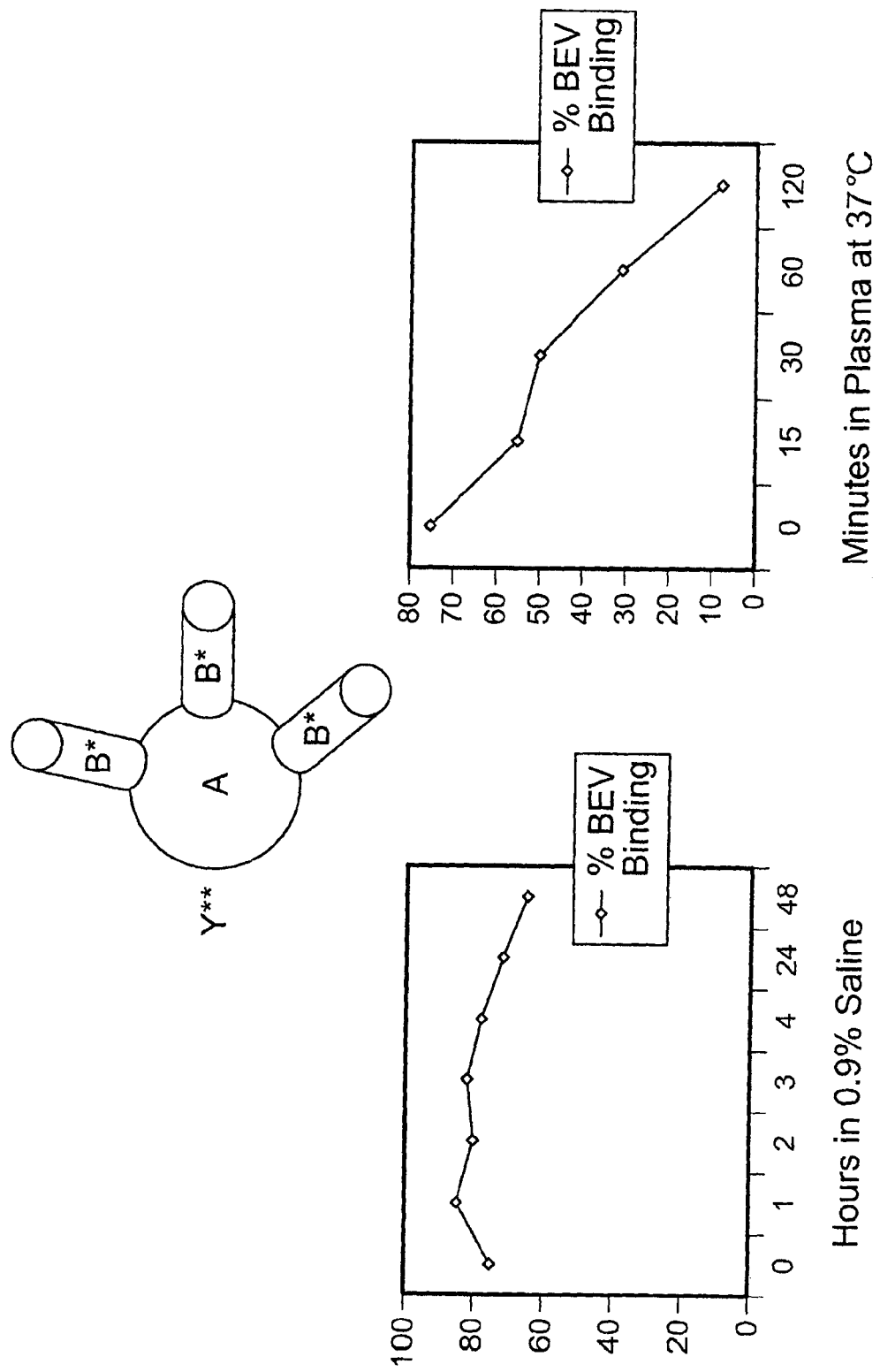
FIG. 12 contains graphs plotting the percent BEV binding for ABX:BEV complexes exposed to 0.9% saline at room temperature or human plasma at 37° C. for the indicated times.

Abraxane®/Avastin® complexes were fluorescently labeled such that both the albumin of the Abraxane® and the bevacizumab were directly labeled with a fluorescent marker. The complexes were visualized by flow cytometry after 0, 1, 2, 3, 4, 24, and 48 hours in 0.9% saline at room temperature and after 0, 15, 30, 60, and 120 minutes in human plasma at 37° C. The complexes were stable in saline at room temperature with only about 10% loss at 24 hours (FIG. 12). In human plasma at 37° C., the complexes began to break down in about 15 minutes and were completely undetectable by 120 minutes.

Example 5

Abraxane®/Cisplatin® Complexes

Figure 13:
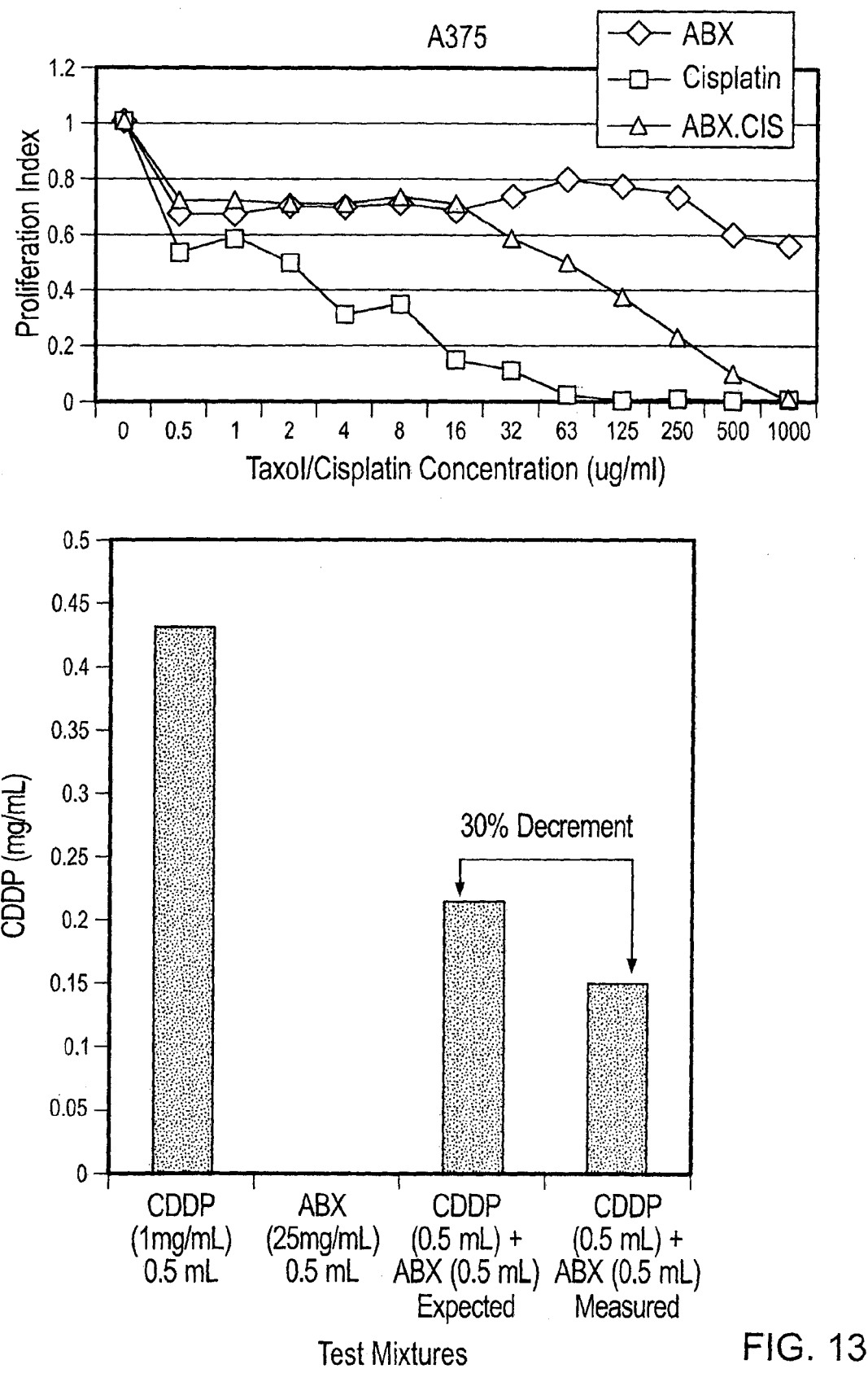
FIG. 13 contains a line graph plotting the proliferation index for A375 cells exposed to Abraxane® (ABX) only, cisplatin only, or Abraxane®:cisplatin complexes at the indicated dose and contains a bar graph plotting demonstrating that 30% of cisplatin (CDDP) remained unbound after ABX:cisplatin were mixed and incubated for 30 minutes.

Abraxane® nanoparticles were incubated with cisplatin (cisplatinum or cis-diamminedichloroplatinum(II) (CDDP)) for 30 minutes at 37° C. The particles were spun, and the supernatant was tested by HPLC to determine how much free cisplatin was in suspension. Cisplatin spontaneously bound to the Abraxane® nanoparticles, and the amount remaining in suspension after the 30 minute incubation with the Abraxane® nanoparticles was only about 30% of the original concentration (FIG. 13). These results demonstrate that about 70% of the cisplatin bound to the Abraxane® nanoparticles.

In another experiment, Abraxane®/cisplatin complexes were generated as described above and added to A375 tumor cells. After an overnight incubation, proliferation of the cells was measured by determining the level of DNA synthesis. The toxicity of the Abraxane®/cisplatin complexes was measured relative to the two drugs individually. The Abraxane®/cisplatin complexes were more toxic to cells (lower level of DNA synthesis) than Abraxane® alone but less toxic than cisplatin alone (FIG. 13). These results demonstrate that cisplatin can be bound to Abraxane® nanoparticles and delivered to tumors without the highly toxic side effects of cisplatin alone.

Example 6

Abraxane®/Antibody Complexes

Figure 14:
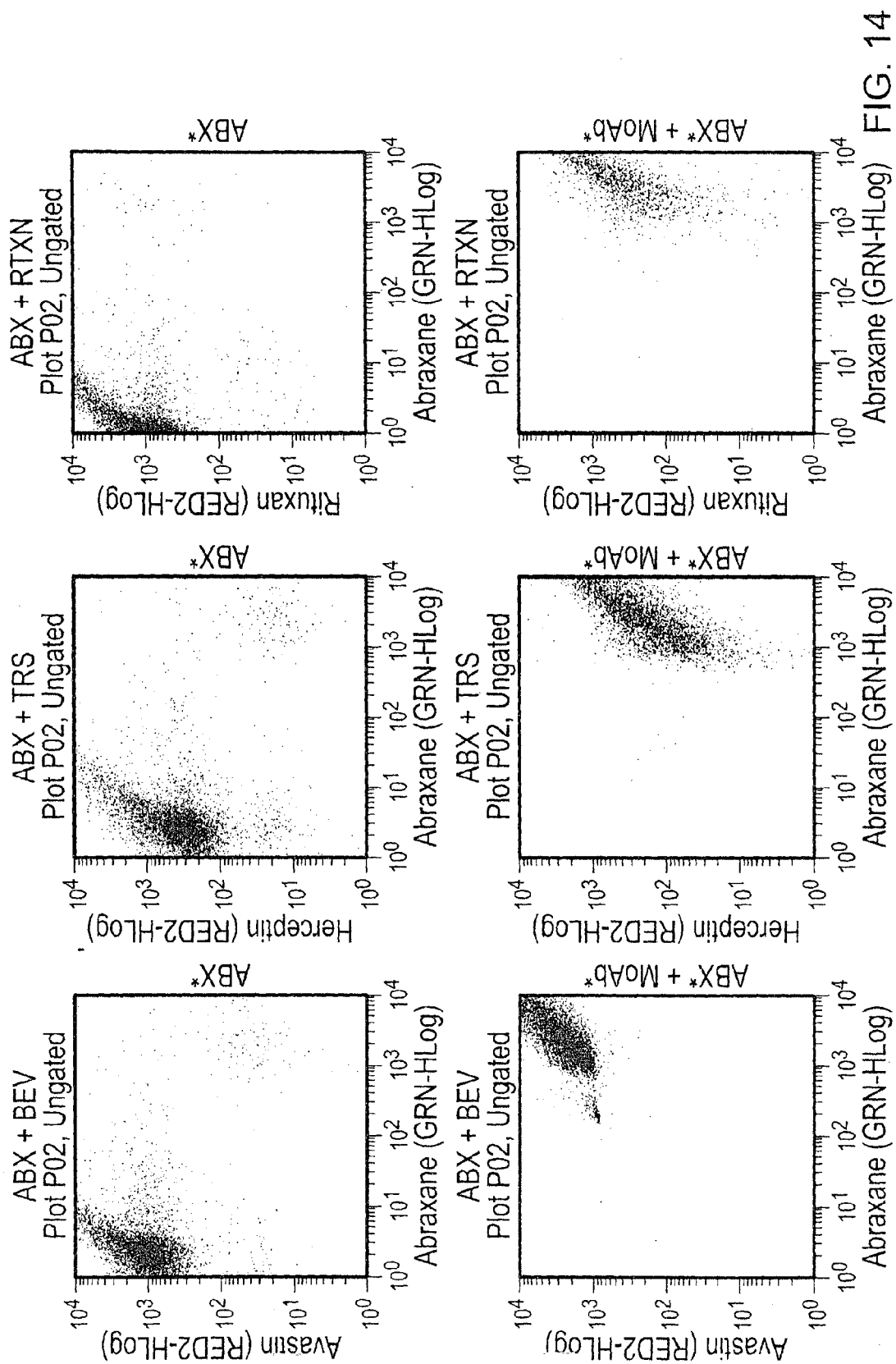
FIG. 14 contains scatter plots of a flow cytometry analysis of the indicated complexes containing Abraxane®.

Three therapeutic monoclonal antibodies (bevacizumab, trastuzamab, and rituxan) were fluorescently labeled and incubated with fluorescently labeled Abraxane® nanoparticles. The particles were spun down, washed, and visualized by flow cytometry. All three of these recombinant therapeutic antibodies spontaneously formed complexes with Abraxane® nanoparticles (FIG. 14). These results demonstrate that albumin-containing nanoparticles can be used to form larger complexes not only with bevacizumab antibodies but also with other antibodies such as trastuzamab and rituxan. Taken together, the results provided herein demonstrate that in vitro mixing of albumin-containing nanoparticles (e.g., Abraxane® nanoparticles) and antibodies (e.g., bevacizumab, trastuzamab, or rituxan) leads to macromolecular complex formation, the characteristics of which (e.g., size, antibody content, or chemotherapeutic drug content) can be customized depending on need. These results also demonstrate that the macromolecular complexes retain antibody mediated target binding specificity, retain or exhibit enhanced chemotherapeutic tumor cell cytotoxicity, and exhibit no additional toxicity beyond that of Abraxane® nanoparticles alone.

Example 7

Abraxane®/Avastin® Complexes Disassociate in Serum

The following was performed to determine what happens to Abraxane®/Avastin® complexes in serum over time. 6 mg or 8 mg of Avastin® were bound to Abraxane® for 30 minutes at room temperature. The complexes were incubated with serum for 15, 30, 45, or 60 minutes. After this incubation, the serum/complex solution was spun down at 10,000 rpm for 10 minutes at 4° C. The supernatants were collected, separated using gel electrophoresis, and analyzed via Western blotting with an anti-paclitaxel antibody and an HRP-conjugated secondary antibody.

Figure 18:
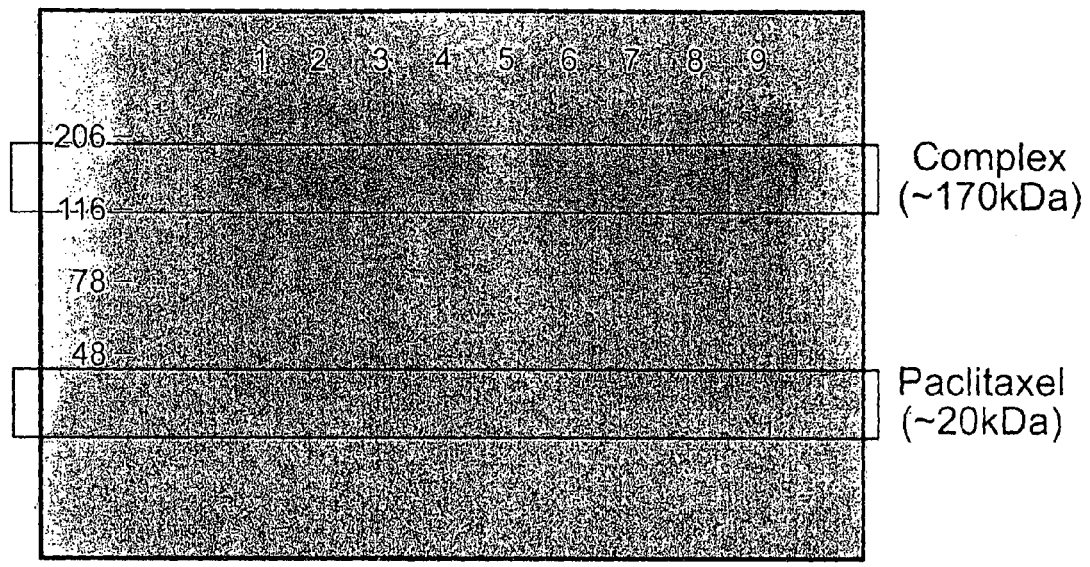
FIG. 18 is a photograph of a Western blot analysis of ABX:BEV complexes exposed to serum for 15, 30, 45, or 60 minutes. The ABX:BEV complexes were formed by incubating either 6 mg or 8 mg of BEV with ABX for 30 minutes at room temperature. The primary antibody used for the Western blot was an anti-paclitaxel antibody. Lane 1: ABX:BEV (6 mg) exposed to serum for 15 minutes; Lane 2: ABX:BEV (6 mg) exposed to serum for 30 minutes; Lane 3: ABX:BEV (6 mg) exposed to serum for 45 minutes; Lane 4: ABX:BEV (6 mg) exposed to serum for 60 minutes; Lane 5: blank; Lane 6: ABX:BEV (8 mg) exposed to serum for 15 minutes; Lane 7: ABX:BEV (8 mg) exposed to serum for 30 minutes; Lane 8: ABX:BEV (8 mg) exposed to serum for 45 minutes; Lane 9: ABX:BEV (8 mg) exposed to serum for 60 minutes.

Incubation in the presence of serum resulted in complex disassociation, not disintegration (FIG. 18).

Example 8

Bevacizumab Does Not Bind Free Paclitaxel

The following was performed to determine if bevacizumab binds free paclitaxel. 4 mg of bevacizumab was incubated with paclitaxel (0.1, 0.5, 1, or 2 mg) for 30 minutes at room temperature. After this incubation, the mixtures were separated using gel electrophoresis and analyzed via Western blotting with an anti-paclitaxel antibody and an HRP-conjugated secondary antibody.

Figure 19:
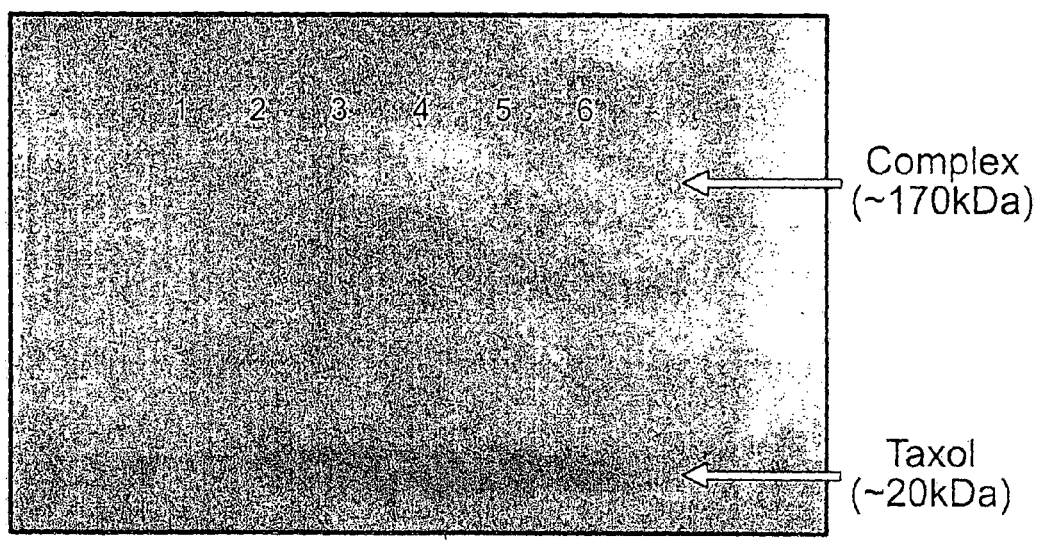
FIG. 19 is a photograph of a Western blot analysis of mixtures of paclitaxel (0.1, 0.5, 1, or 2 mg) and BEV (4 mg) incubated together for 30 minutes at room temperature. The primary antibody used for the Western blot was an anti-paclitaxel antibody. Lane 1: Bev (4 mg); Lane 2: Taxol (2 mg); Lane 3: Taxol (2 mg)+Bev (4 mg); Lane 4: Taxol (1 mg)+Bev (4 mg); Lane 5: Taxol (0.5 mg)+Bev (4 mg); Lane 6: Taxol (0.1 mg)+Bev (4 mg).

Bevacizumab did not bind free paclitaxel (FIG. 19).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer in a mammal, which method comprises:
   (a) obtaining a dry composition of preformed nanoparticle complexes comprising albumin-bound paclitaxel and bevacizumab at a ratio of up to 5:1;
   (b) forming an aqueous composition of said dry composition, said aqueous composition being suitable for injection into a mammal having cancer, and
   (c) administering to said mammal an effective amount of said aqueous composition wherein said administration treats said cancer and further wherein said preformed nanoparticle complexes retain antibody mediated target binding specificity.

2. The method of claim 1, wherein said mammal is a human.

3. The method of claim 1, wherein said cancer is skin cancer.

4. The method of claim 3, wherein said skin cancer is stage IV melanoma.

5. The method of claim 1, wherein said preformed nanoparticle complexes comprise an alkylating agent.

6. The method of claim 1, wherein said administration of said injectable composition is by intravenous drip.

* * * * *